United States Patent [19]

Ryan et al.

[11] Patent Number: 4,766,110

[45] Date of Patent: Aug. 23, 1988

[54] NOVEL COMPLEX AMIDO AND IMIDO DERIVATIVES OF CARBOXYALKYL PEPTIDES

[76] Inventors: James W. Ryan, 3420 Poinciana Ave., Miami, Fla. 33133; Alfred Chung, 8781 SW. 87th St., Miami, Fla. 33125

[21] Appl. No.: 925,232

[22] Filed: Oct. 31, 1986

Related U.S. Application Data

[63] Continuation-in-part of Ser. No. 295,137, Aug. 21, 1981, abandoned.

[51] Int. Cl.[4] .................... A61K 37/02; C07D 207/00; C07D 277/04; C07D 275/02; C07D 279/00; C07D 265/00; C07D 239/02; C07D 265/30; C07D 233/30; C07D 231/10; C07D 231/06; C07D 231/00; C07D 207/12; C07D 293/00; C07D 207/10; C07D 233/66; C07D 279/10; C07D 211/60; C07D 211/78

[52] U.S. Cl. ....................................... 514/19; 548/953; 548/533; 548/201; 548/214; 548/551; 548/556; 548/100; 548/557; 548/488; 548/343; 548/320; 548/378; 548/379; 548/356; 544/63; 544/335; 544/172; 544/58.2; 544/3; 546/245; 546/326

[58] Field of Search .......................... 530/800; 514/19; 548/953, 533, 201, 214, 551, 556, 100, 557, 188, 343, 320, 378, 379, 386; 544/3, 63, 335, 172, 58.2; 546/245, 326

[56] References Cited

U.S. PATENT DOCUMENTS

| | | | |
|---|---|---|---|
| 4,374,829 | 2/1983 | Harris et al. | 530/800 |
| 4,456,595 | 6/1984 | Weller, III et al. | 530/800 |
| 4,470,972 | 9/1984 | Gold et al. | 514/19 |
| 4,470,973 | 9/1984 | Natarajan et al. | 530/800 |
| 4,512,979 | 4/1985 | Patchett et al. | 530/800 |
| 4,513,009 | 4/1985 | Roques et al. | 514/513 |
| 4,514,391 | 4/1985 | Gordon et al. | 530/800 |
| 4,525,301 | 6/1985 | Henning et al. | 530/800 |
| 4,555,502 | 11/1985 | Patchett et al. | 530/800 |
| 4,556,655 | 12/1985 | Andrews et al. | 530/800 |
| 4,558,038 | 12/1985 | Skiles et al. | 530/800 |
| 4,587,234 | 5/1986 | Gordon et al. | 530/800 |
| 4,587,258 | 5/1986 | Gold et al. | 514/412 |

FOREIGN PATENT DOCUMENTS

| | | |
|---|---|---|
| 0038758 | 10/1981 | European Pat. Off. . |
| 0054862 | 4/1982 | European Pat. Off. . |
| 0050800 | 6/1982 | European Pat. Off. . |
| 2095682 | 10/1982 | United Kingdom . |

*Primary Examiner*—Delbert R. Phillips

[57] ABSTRACT

Novel inhibitors of angiotensin converting enzyme are disclosed which have the general formula

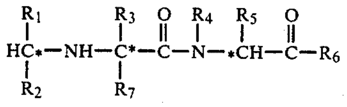

wherein $R_1$ and/or $R_3$ form complex amides and imides thereof, $R_4$ and $R_5$ form with —N—C— a 4–6 membered ring structure as described and the other R substituents are selected from a variety of disclosed groups.

15 Claims, No Drawings

NOVEL COMPLEX AMIDO AND IMIDO DERIVATIVES OF CARBOXYALKYL PEPTIDES

This application is a continuation-in-part of Ser. No. 06/295,137, filed Aug. 21, 1981, now abandoned.

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence AspArgValTyrIleHisProPheHisLeu to an octapeptide, angiotensin II, by removal of the carboxy-terminal HisLeu. The symbols for the foregoing chemical moieties and others used throughout this application are explained in the following table:

Arg=arginine
Asp=aspartic acid
Boc=t-butyloxycarbonyl
Cbo=carbobenzyloxy
<Glu=L-pyroglutamic acid
Gly=glycine
Hip=Hippuric acid (Benzoyl-glycine)
His=histidine
Ile=isoleucine
Leu=leucine
Phe=phenylalanine
Pro=proline
ΔPro=3,4-dehydroproline
Ser=serine
Tos=Tosyl
Trp=tryptophan
Tyr=tyrosine
Val=valine
Pht=phthaloyl
ACE=angiotensin converting enzyme
Hepes=N-2-hydroxyethylpiperazine-N'-2-ethanesulfonic acid In each instance the symbol for any amino acid is also used herein at times to refer to a mono-or-di-valent radical of such acid and those of ordinary skill in the art will readily understand the context of each specific use.

Angiotensin I is formed by the action of the enzyme renin, an endopeptidase found in kidney, other tissues, and plasma, on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. [Gavras, I. et al., *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked α-carboxyl group. The action of ACE results in hydrolytic cleavage of the penultimate peptide bond from the carboxyl-terminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry,* 2nd Ed., Worth Publishers, Inc., New York, 1975, pp. 189–195. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide $BPP_{5a}$ (also called SQ20475) from snake venom, whose sequence is <GluLysTrpAlaPro.

Numerous synthetic peptide derivatives have been shown to be ACE inhibitors by Ondetti, et al. in U.S. Pat. No. 3,832,337, issued Aug. 27, 1974.

The role of ACE in the pathogenesis of hypertension has prompted a search for inhibitors of the enzyme that could act as antihypertensive drugs. See for example U.S. Pat. Nos. 3,891,616, 3,947,575, 4,052,511 and 4,053,651. A highly effective inhibitor, with high biological activity when orally administered, is D-3-mercapto-2-methylpropanoyl-L-proline, designated SQ14225, or "captopril" disclosed in U.S. Pat. No. 4,046,889 to Ondetti et al., issued Sept. 6, 1977, and in scientific articles by Cushman, D. W. et al., *Biochemistry* 16, 5484 (1977), and by Ondetti, M. et al., *Science* 196, 441 (1977). The inhibitor SQ14225 reportedly has an $I_{50}$ value of $2.3\times10^{-8}$M. The $I_{50}$ value reported by Cushman, et al., supra is the concentration of inhibitor required to produce 50% inhibition of the enzyme under a standard assay system containing substrate at a level substantially above $K_m$. It will be understood that $I_{50}$ values are directly comparable when all potential factors affecting the reaction are kept constant. These factors include the source of enzyme, its purity, the substrate used and its concentration, and the composition of the assay buffer. All $I_{50}$ data reported herein have been performed with the same assay system and same enzyme (human urinary ACE) and with the same level of substrate and are therefore internally consistent.

The mode of action of SQ14225 has been based upon a model of the active site of ACE developed by analogy with the better known related enzyme, carboxypeptidase A. The active site was postulated to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and a S-acetyl derivative, substantially reduced potency of the inhibitor. See Cushman, D.W. et al., *Biochemistry, supra.*

In vitro study of the mechanism by which SQ14225 and its analogs act to inhibit ACE has been somewhat hampered by the instability of these molecules under ambient conditions. For example, it has been observed that a fresh aqueous solution of concentration, e.g., 1 mg per ml of SQ14225 at a pH of about 8 becomes substantially less active upon standing for as little as 30 minutes, and that activity continues to decrease as the solution stands for longer periods. It is believed that this loss in activity is mainly the result of dimerization of SQ14225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ14225 on standing is in some part a consequence of one or more such oxidation reactions, with formation of a sulfone or sulfoxide which does not function effectively as an inhibitor for ACE.

Such reports of SQ14225 clinical testing as are currently available, some of which refer to the compound under the name "Captopril" or "Capoten", suggest that the product is sufficiently stable in the normal gastric and intestinal environments of most patients to be an effective inhibitor of ACE when administered orally. It is not yet clear, however, whether there may be a group of patients for which SQ14225 is substantially ineffective. Because of the high reactivity of the free sulfhydryl group, SQ14225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras, et al., *New England J. Med.* 298, 991 (1978). Disulfides and oxidative degradation products of SQ14225, if formed, may at best be expected to be largely ineffective as inhibitors. It may be postulated accordingly that dose response to SQ14225 may vary with conditions of administration and among individual patients. Moreover, in at least some patients, unwanted side effects may occur and maintenance of an effective concentration of the inhibitor in the body may be difficult to control.

Adverse effects of SQ14225 in man include fevers and rashes. (Gavras et al., supra). Hoorntje et al., *The Lancet* i., 1212–1214 (1980) describe the performance of renal biopsies on 13 patients treated with SQ14225. All biopsies showed evidence of immune complex deposition along the glomerular basement membranes, although 9 of 13 patients were asymptomatic at the time of the biopsy. These authors also discussed similarities of their findings with those induced by another drug with a free mercapto group, D-penicillamine.

In an effort to devise better inhibitors of angiotensin converting enzyme that are more stable than captopril and less likely to induce D-pencillamine-like adverse effects, applicants have prepared a series of compounds having side chain structure analogous to an effective substrate for the enzyme, benzoyl-Phe-Ala-Pro, and disclosed them in copending U.S. application Ser. No. 187,992 filed Sept. 17, 1980 (abandoned). Also relevant are the class of carboxylalkyldipeptide derivatives disclosed in European published application of Patchett et al., published on or about June 25, 1980. The present application defines compounds such as N-[L-1-carboxy-3-(carboanilide)propyl]-D,L-Ala-L-Pro, N-[L-1-carboxy-3-(carbo-4-iodoanilide)propyl]-D,L-Ala-L-Pro, and analogs i.e., amides and imides of N-(lower alkylene) Ala-Pro. These two named compounds were found to be unexpectedly effective in inhibiting angiotensin converting enzyme in vitro, that is they have a very low $I_{50}$, in the order of $10^{-9}$M. In contrast, another closely related analog of the two named compounds, i.e., N-[L-1-carboxy-2-(carbopyrrolide)ethyl]-D,L-Ala-Pro, was found to have a much higher $I_{50}$, in the order of $10^{-7}$M, a potency of inhibitor likely to be too low for antihypertensive effectiveness. It is believed, therefore, that amides and imides of N-(lower alkylene)-Ala-Pro and related compounds have unpredictable effects on angiotensin converting enzyme.

In addition, the removal of iodine from N-[L-1-carboxy-3-(carbo-4-iodoanilide)propyl]-D,L-Ala-L-Pro increases intravenous effectiveness three-fold, an unexpectedly large difference in the in vitro effect of the anti-hypertensive compounds of this invention. Hence, amides and imides of N-(lower alkylene)-D,L-Ala-Pro and related compounds are new agents with surprising effectiveness in lowering blood pressure in vivo.

Moreover, since the compounds of this invention do not have the free sulfhydryl group of SQ14225, they are most likely to be stable and have durations of action much longer than that of SQ14225. Thus, inhibitors of this invention may be used for treating hypertension with less frequent dosage schedules than required for SQ14225 and may be capable of administration under less rigorously controlled conditions.

BRIEF DESCRIPTION OF THE INVENTION

Novel inhibitors of ACE are disclosed which have the general formula

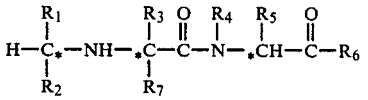

wherein $R_2$ is COOH, $CH_2COOH$, COSH, $CH_2COSH$, $CH_2SH$, $CH_2CH_2SH$, a physiologically acceptable nontoxic salt of any of them, COOY, $CH_2COOY$, COSY, $CH_2SY$, or $CH_2CH_2SY$ wherein Y is phenyl, benzyl or a 1-5 carbon alkyl group; or

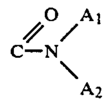

wherein either of $A_1$ and $A_2$ may be H, phenyl, benzyl or a 1-5 carbon alkyl group;

$R_4$ and $R_5$ together form a ring with the nitrogen and carbon atoms to which they are respectively attached, which ring is one of the structures:

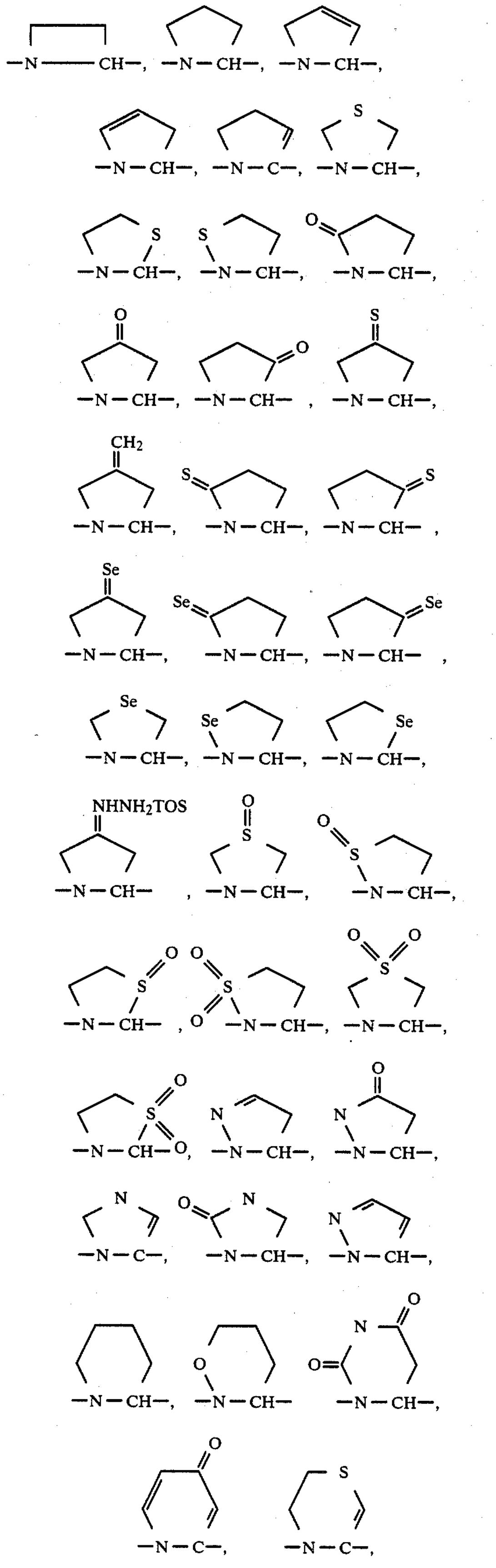

-continued

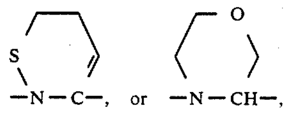

it being understood that any of these structures may be monosubstituted with —OH, —$OCH_3$, F,

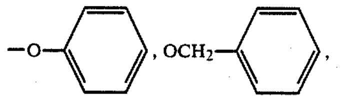

Cl, Br, I, phenyl, hydroxyphenyl, —SH, —$SCH_3$,

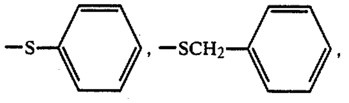

—$NHCH_3$, —$CH_2NH_2$, —$CH_3$, —$CH_2OH$, propyl, guanidino, nitroguanidino or thioguanidino and that any of the 5- or 6-membered rings may be disubstituted with —OH, F, Cl, Br, I, $OCH_3$ or any combination of two of this group of substituents;

$R_6$ is —OM or —SM, wherein M may be H, an alkyl group of 1-3 carbon atoms or any other ester moiety hydrolyzable under mammalian in vivo conditions to —OH, or an ionically bonded anion of a physiologically acceptable nontoxic salt;

$R_7$ is H—, $CH_3$—, halomethyl, hydroxymethyl, aminomethyl or mercaptomethyl;

and

A. $R_1$ and $R_3$ may each be of the general fomula

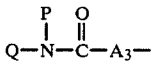

wherein $A_3$ is:

(i) alkylene of 1-6 carbons, branched chain alkyl of 1-6 carbons, cycloalkyl alkylene, alkylcycloalkylalkylene, or alkylcycloalkylene;

(ii) aralkylene wherein the alkyl group is 1-6 carbons or alkylaryl;

(iii) phenyl;

(iv) alkylaralkylene wherein the alkyl groups may be the same or different and are 1-6 carbons in length;

(v) substituted alkylene, substituted branched chain alkyl, substituted cycloalkylalkylene, substituted alkyl cycloalkylalkylene, substituted alkylcycloalkylene, substituted alkylaryl, substituted aralkylene, substituted phenyl or substituted alkylaralkylene wherein the substituent or substituents may be the same or different, may be included in an alkylene chain or pendent thereto, and are selected from amino, halo, hydroxy, mercapto, $NO_2$, carboxy, $CONH_2$, lower alkyl, halomethyl, hydroxymethyl, aminomethyl, dihalomethyl, trihalomethyl, cyano, mercaptomethyl, methoxymethyl, methylthiomethyl, methoxycarbonylmethyl, cyanomethyl, benzyl, acetoxymethyl, $CH_2$=CH—$CH_2$—, isobutyl, mercaptoalkyl of 2-3 carbon atoms, hydroxyalkyl of 2-3 carbon atoms, acetylthioethyl, benzamido, acetamido, phthaloylaminoalkylene wherein the alkylene group has 1–4 carbon atoms, -alkoxycarbonyl isoalkylene wherein the alkyl group contains 1–5 carbons and the isoalkylene group contains 3–5 carbons, benzoylamino, alkanoylamino of 1–5 carbons, alkylamide of 1–5 carbons, phenylamine, alkylamine of 1–5 carbons, lower alkoxy, aryloxy, lower alkylamino, diloweralkylamino, acylamino, arylamino, guanidino, imidazolyl, indolyl, lower alkylthio, arylthio, carboxy amido and carbolower alkoxy;

(vi) alkylenethio- or alkylenethioalkylene of 1–6 carbons, alkylthioalkylene of 1–6 carbons;

(vii) alkyleneoxy or alkyleneoxyalkylene wherein the alkyl groups may be the same or different and are 1–6 carbons;

(viii) alkoxyphenyl or alkoxybenzyl in which the alkoxy group has 1–3 carbons, phenoxyphenyl, phenoxybenzyl, benzyloxybenzyl or benzyloxyphenyl or a thioether analog of any of them;

(ix)

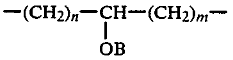

wherein n=0–4, m=0–4, and B=H or a 1–5 carbon alkyl group; or an —SB analog thereof;

(x)

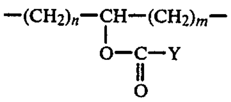 or 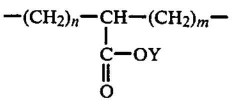 or

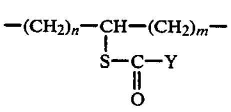 or 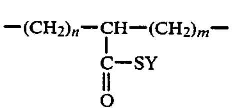

wherein n and m have the same significance as above, Y is phenyl, benzyl or a 1–5 carbon alkyl group;

(xi)

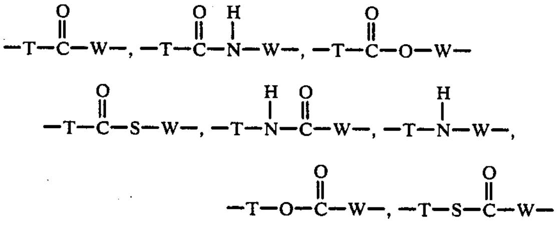

wherein T and W may be the same or different and are alkylene, aryl, benzyl or cycloalkyl, and P and Q may be the same, or one of them may be H or they may combine to form a ring with the nitrogen to which they are attached.

Either or both of P and Q may be selected from any of the following:

(a) $C_1$–$C_6$ straight or branched chain alkyl groups or $C_1$–$C_6$ straight or branched chain alkenyl groups, any one of which may be substituted with any of halo, hydroxy, alkoxy, aryloxy, amino, alkylamino, dialkylamino, alkylacylamino, arylamino, guanidino, thioguanidino, nitroguanidino, hydrazino, ureido, nitro, mercaptocarbonyl, hydroxyamino, histidinyl, cyano, imidazolyl, indolyl, mercapto, alkylthio, arylthio, carboxy amido or carboalkoxy, wherein the alkyl groups contain 1–6 carbon atoms;

(b) cycloalkyl or cycloalkyl alkylene wherein cycloalkyl has 4–12 carbons, and alkylene 1–5 carbons, which may be substituted with any of —OH, —SH, halo, COOH, COSH, $CONH_2$, $NO_2NH_2$, $NO_2$, $CH_3$, —$OCH_3$, —$SCH_3$,

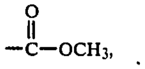

hydrazino, ureido, hydroxyamino, cyano, guanidino, thioguanidino or nitroguanidino groups;

(c) aralkyl or alkaryl groups which may be ring substituted with one or more of the following:

SH, halo, $CH_2COOH$, $CH_2CONH_2$, $CH_2CONH$-alkyl, COSH, COOH, $CONH_2$, CONH-alkyl, $CH_2COSH$, $CH_2SH$, $CH_2OH$, OH, $NO_2$, amino, alkyl, alkoxy, aralkyloxy, alkylthio, and aralkylthio groups, wherein the alkyl groups contain 1–6 carbons and may also or alternatively be chain substituted with —$CH_3$, —OH, —$OCH_3$, halo, —$SCH_3$,

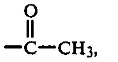

—$NH_2$, —$NO_2$, —CN, —SH, —NHOH, —$NHNH_2$,

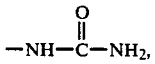

or a thio or nitro derivative thereof, —COOH or COSH;

(d) an aryl, heterocyclic or adamantanyl group which may be ring-substituted with at least one group selected from halo, —OH, —O—alkyl, —O—aryl, $NH_2$, NH-aklyl, N-(alkyl)$_2$,

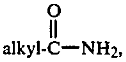

aryl—$NH_2$, guanidino, thioguanidino, nitroguanidino, hydrazino, ureido, nitro, mercaptocarbonyl, hydroxyamino, cyano imidazolyl, indanyl, histidinyl, —SH, —S—alkyl, S—aryl,

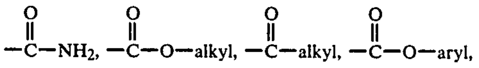

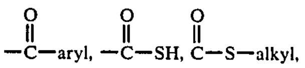

—C—S—aryl and —$NO_2$ when P and Q join with N to form a ring, the ring may be any 4–10 membered heterocyclic ring which contains a nitrogen with only two of its valences attached to other ring members, B. Alternatively, $R_1$ may be

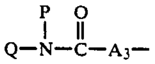

and $R_3$ may be (i) mono—N substituted alkylene of 2-4 carbons wherein the N substituent is benzoyl, Boc, CbO, Tos, formyl or acetyl;

(ii) hydroxyphenyl or hydroxyphenyl-(1-6C)-alkylene or a thiol analog of either;

(iii) mercaptoalkylene of 1-6 carbons;

(iv) phenylalkylene wherein the alkylene group has 1-6 carbons;

(v) phenylthioalkylene or benzylthioalkylene wherein the alkylene group has 1-6 carbons;

(vi) alkylthioalkylene wherein the alkyl and alkylene groups have 1-3 carbons;

(vii) alkoxyphenyl or alkoxybenzyl in which the alkoxy group has 1-3 carbons, phenoxyphenyl, phenoxybenzyl, benzyloxybenzyl or benzyloxyphenyl or a thioether analog of any of them;

(viii)

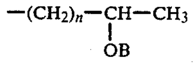

wherein n=0-4 and B=H or a 1-6 carbon alkyl group; or an —SB analog thereof;

(ix) $(CH_2)_pCOOZ$ or $(CH_2)_p$ COSZ wherein p=0-3 and Z is H, phenyl, benzyl, a 1-5 carbon alkyl group, or an anion of a physiologically acceptable salt;

(x)

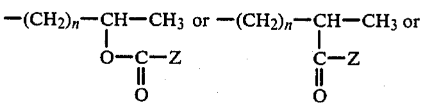

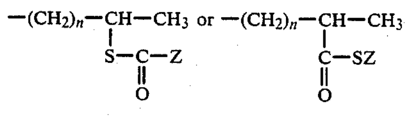

wherein n is 0 to 4 and Z each have the same significance as above;

(xi)

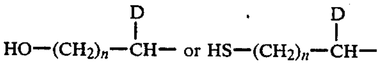

wherein n=0-4, D is phenyl, thienyl or a 1-3 carbon alkyl group;

(xii) HO—$(CH_2)_n$—$C(CH_3)_2$—, HS—$(CH_2)_n$—$C(CH_3)_2$—, p-hydroxyphenyl—$(CH_2)_n$—$C(CH_3)_2$— or —p-mercaptophenyl—$(CH_2)_n$—$C(CH_3)_2$— wherein n has the same significance as above;

(xiii) p-mercaptophenyl—$(CH_2)_n$—$CH_2$— or p-hydroxyphenyl—$(CH_2)_n$—$CH_2$—wherein the phenyl ring has one or two nitro or amino substituents and n has the same significance as above;

(xiv)

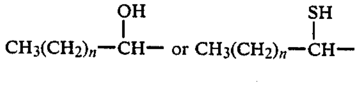

wherein n has the same significance as above;

(xv) $NH_2$—alkylene or $NO_2$—alkylene containing one hydroxy or mercapto substituent and having 1-6 carbon atoms;

(xvi) hydroxy- or mercapto-phenoxybenzyl;

(xvii)

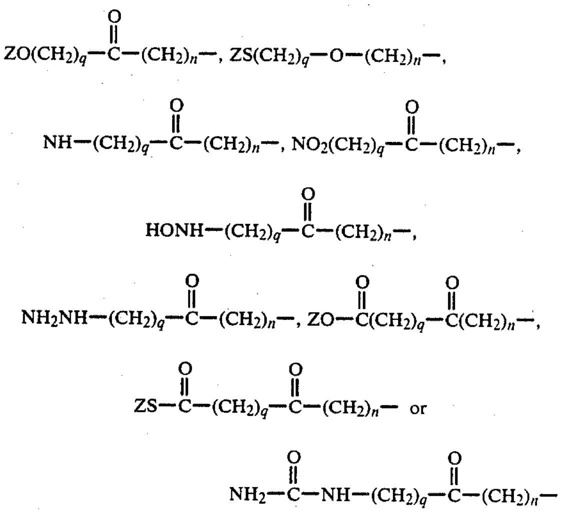

wherein q=1-5 and n is from 0 to 4 and Z has the same significance as above;

(xviii)

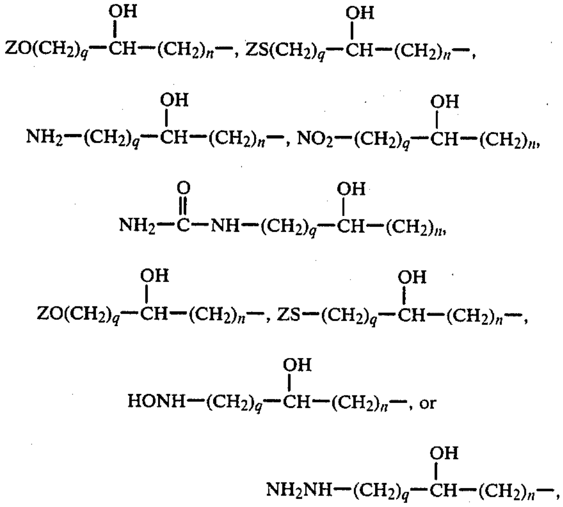

wherein q and n all have the same significance as above;

(xix)

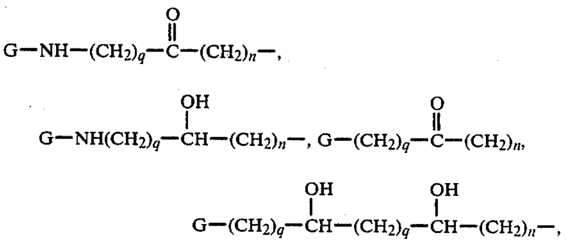

wherein G is an alkacyl or alkacyloxy group of 1-6 carbons, a benzoyl or benzoyloxy group, or a phenylalkacyl or phenyl-alkacyloxy group wherein the alkacyl or alkacyloxy group contains 2-6 carbons and q and n have the same significance as set forth above;

(xx)

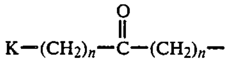 or 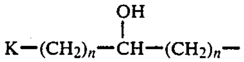

wherein n has the significance stated above and K is selected from carboxyphenyl, aminophenyl, nitrophenyl, halophenyl, hydroxyphenyl, alkylthiophenyl, alkylphenyl, mercaptophenyl, cyanophenyl, mercaptocarbonylphenyl, alkylcarbonylphenyl, alkylcarbonyloxyphenyl, hydrazinophenyl, ureidophenyl, alkylcarbonylaminophenyl, alkylcarbonylthiophenyl, alkyloxyphenyl and hydroxy-aminophenyl, wherein all alkyl groups contain 1-6 carbon atoms;

(xxi)

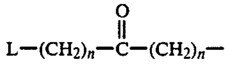 or 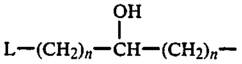

wherein n has the significance stated above and L is selected from cycloalkyl groups of 3-7 carbons which may be unsubstituted or substituted with up to two groups selected from among carboxy, amino, nitro, halo, hydroxy, mercapto, mercaptocarbonyl, hydroxyamino, alkyl, alkylcarbonyl, alkylcarbonyloxy, alkylthio, alkylcarbonylamino, alkylcarbonylthio, cyanohydrazino, ureido and alkyloxy, wherein all alkyl groups contain 1-6 carbon atoms;

(xxii) guanidino alkylene, thioguanidinoalkylene, or nitroguanidino alkylene in which the alkylene groups contain 1-6 carbon atoms;

(xxiii) ring substituted aryl groups in which the ring substituents may be the same or different and may comprise up to five per ring of the following: —$NH_2$, —OZ, —SZ, halogen, —CN, —$NO_2$, —COOZ, —COSZ, $CONH_2$, —$NHNH_2$, alkyl, alkylcarbonyl, alkylcarbonyloxy, alkylcarbonylamino, haloalkyl, dihaloalkyl, trihalomethyl, hydroxyamino, alkylcarbonylthio, phenoxy, and benzyloxy wherein the alkyl groups contain 1-6 carbon atoms and z has the same significance as above;

(xxiv) amidoalkylene or alkylcarbonyl-aminoalkylene wherein the alkyl and alkylene groups contain 1-6 carbon atoms;

(xxv) hydroxyaminoalkylene of 1-6 carbons;

(xxvi) vinyl and substituted vinyl groups in which the substituents may be alkyl, aryl, cycloalkyl or heterocyclic groups;

(xxvii) unsubstituted heterocyclic groups from among phenothiazinyl, pyrrolidinyl, pyrrolyl, quinolinyl, imidazolyl, pyridyl, thyminyl, benzothiazinyl, indolyl, thienyl, purinyl, piperidinyl, morpholinyl, azaindolyl, pyrazinyl, pyrimidyl, piperonyl, piperazinyl, furanyl, thiazolyl and thiazolidinyl, cytosinyl;

(xxviii) alkylene or alkenyl groups of 1-6 carbons substituted with one of the heterocyclic rings from (xxvii) above;

(xxix) groups from (xxvii) or (xxviii) above containing up to four ring substituents on the heterocyclic ring selected from among —OZ, —SZ, —COOZ, —$NO_2$, —$NH_2$, —COSZ, halogen, haloalkyl, dihaloalkyl, trihalomethyl, cyano, $CONH_2$, alkyl, alkylcarbonyl, alkylcarbonyloxy, alkylcarbonylamino, alkylcarbonylthio, phenoxy, benzyloxy,

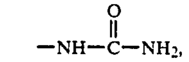

—$NHNH_2$ and HONH—, wherein Z has the same significance as above;

(xxx) groups from (xxvii), (xxviii) or (xxix) attached to one valence of an etheric —O— or —S—;

(xxxi) mono-, di- or tri-alkyl, alkenyl- or phenyl-silyl or -selenyl wherein the alkyl or alkenyl groups contain 1-6 carbons;

(xxxii) any of H, 1-5 carbon straight or branched chain alkyl, phenyl, —OH, alkoxy of 1-6 carbons, benzyloxy, benzyloxyalkylene or phenoxyalkylene wherein the alkylene has 1-5 carbons, alkoxyalkylene having 1-5 carbons in the alkoxy and alkylene groups, aminoalkylene of 1-6 carbons, alkenyl of 1-6 carbons, benzyl, hydroxyalkyl of 1-6 carbons, mercaptoalkyl of 1-6 carbons, histidinyl, haloalkyl of 1-6 carbons, 4-aminomethyl-benzyl, acetamidoalkyl of 1-5 carbons, benzylthiomethylene, or dimethylaminoalkyl of 1-5 carbons.

C. Alternatively, $R_3$ may be

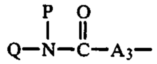 and and $R_1$ may be any of groups (i)-(xxxi) above or any of H, $C_1$-$C_8$ straight or branched chain alkyl, phenyl, benzyl, unsubstituted aminoalkylene of 2-6 carbons, hydroxyalkylene of 1-6 carbons, hydroxyphenyl, phenoxyalkylene or benzyloxyalkylene wherein the alkylene group has 1-6 carbons, cycloalkyl of 3-6 carbons, cycloalkyl methyl, 3-indolyl-, phenylethyl, methylthioethyl, 3-indolyl alkyl wherein the alkyl group contains 1-5 carbons, imidazolyl, imidazolylalkyl wherein the alkyl group contains 1-5 carbons, phenoxymethyl, phenylthiomethyl, 4-aminomethyl benzyl, 2-aminophenethyl, naphthylethyl, 4-halophenethyl, 3,4-dihalophenethyl or phenoxyphenethyl, or $R_1$ and $R_2$ together may form with —CH a lactone ring of the formula:

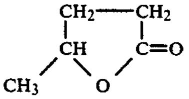 or 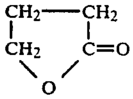

or an analogous six-membered ring.

In the general formula above, asterisks indicate possible asymmetric centers. These centers may be racemized or in any optically active form. However, the S-form is preferred.

The inhibitors are useful as orally effective antihypertensive agents.

DETAILED DESCRIPTION OF THE INVENTION

The present invention in its broad aspects relates to secondary amino compounds containing at least one amino acid or related structure containing the sequence

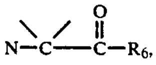

preferably

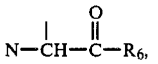

and includes at least one group of the general formula

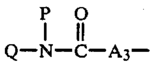

in the $R_1$ or $R_3$ position.

The compounds of this invention may be made in a variety of ways. For example, an alpha keto carboxylic acid of the general formula

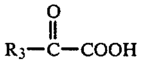

may be coupled to

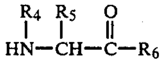

to give a product

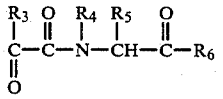

using a conventional coupling agent such as dicyclohexylcarbodiimide ("DCC") or diphenylphosphorylazide ("DPPA"). This product in turn may be coupled, in the presence of a reducing agent such as sodium cyanoborohydride to a compound of the general formula

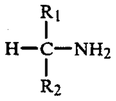

to give the desired compound.

In such an instance

may, e.g. be first reacted with an appropriate ω-carboxylated compound, e.g.,

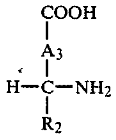

to yield

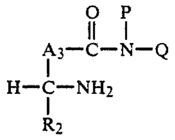

In this particular scheme, e.g.,

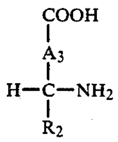

may alternatively first be coupled with

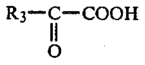

and the product then coupled with

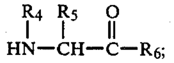

in such instance

may be reacted with the —COOH attached to $A_3$ after the first or second coupling step. Similarly,

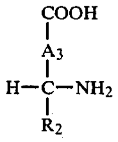

may be coupled to

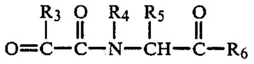

and Q—N—P may then be reacted with the COOH adjacent to $A_3$. As those of ordinary skill inthe art will readily understand, conventional blocking groups such as BOC, CbO, etc. may be introduced at appropriate stages to protect reactive groups and may be removed when protection is no longer needed or wanted.

It is within ordinary skill, e.g., to use in lieu of

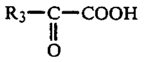

a compound

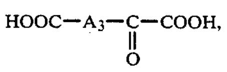

protect either of the COOH groups as desired in the particular reaction scheme preferred and prepare,

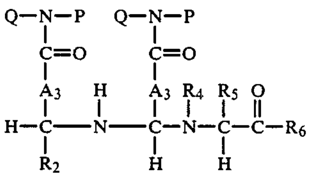

Similarly if

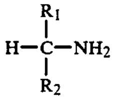

wherein $R_1$ is other than

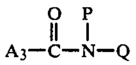

is chosen and

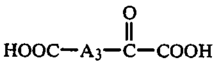

is used in lieu of

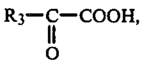

the reactions may be manipulated with appropriate blocking and coupling steps to yield a product

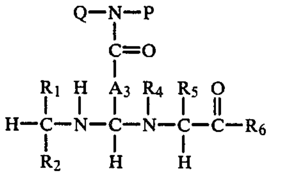

Among suitable ω-carboxylic acids of the general formula

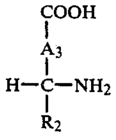

are

- 2-amino malonic acid 1-ethyl ester
- 2-amino adipic acid 1-ethyl ester
- 2-amino pimelic acid 1-ethyl ester
- 2-amino suberic acid 1-ethyl ester
- 2-amino azelaic acid 1-ethyl ester
- 2-amino sebacic acid 1-ethyl ester and others which will readily occur to those of ordinary skill in the art.

These acids may be purchased in many instances from e.g. Aldrich Chemical Co. or Chemical Dynamics Co.

It is also well known that α-amino acids of the formula

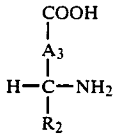

wherein $R_2$ is COOH or another carboxyl function may be obtained from α-keto dicarboxylic acids using methods described by Waters, K. L., *Chem. Rev.* 41, 585-98 (1947).

Among suitable compounds of the general formula

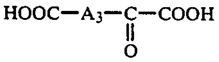

referred to above are:

- α-keto glutaric acid
- oxalacetic acid
- ketomalonic acid
- para-carboxy phenyl pyruvic acid
- indole-1-carboxy-3-pyruvic acid
- 2-ketoadipic acid Other examples of suitable compounds are 4-keto pimelic acid and β-carboxy-DL-lactic acid.

It is to be understood that when $R_3$=

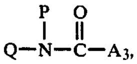

the compound of the general formula

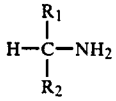

can be selected from a very wide group.

Suitable $R_1$ comounds of the general formula

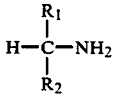

for use in making the compounds of the invention include, but are not limited to compounds within the scope of said formula and selected from tert. leucine, 2-methylglutamic acid, α-amino-γ-guanidino butyric acid, α-amino-β-guanidinopropionic acid, β-fluorophenylalanine, β-hydroxyvaline, α-oxalysine, 3-hydroxy ornithine, $N^{\epsilon}$-hydroxylysine, $N^{\delta}$-methyl arginine, $N^{\delta}$-hydroxyarginine, canvanin, 5,5$^1$-dihydroxyleucine, β-carboxyaspartic acid, β-fluoroaspartic acid, β-methyl-aspartic acid, β-methylene aspartic acid, p-amido phenylalanine, p-guanidinophenylalanine, p-methyl-phenylalanine, 2-ethoxy-5-nitrophenyl-alanine, 2-hydroxy-5-nitrophenylalanine, 4-mercaptophenylalanine, 2-amino-2-indoleacetic acid, 2-amino-3-adamantyl propionic acid, β-methylene norvaline, α-amino-4-(4-carboxythiazolyl)-butyric acid) 3-chloroglutamic acid, α-amino-γ-nitrovaleric acid, 4-azalysine, β-(2,4,5-trihydroxyphenyl)alanine, β(3-bromo-5-methoxyphenyl)alanine, β-(3,5 dimethyl-4 methoxyphenyl)alanine, 3,5-di(ethylthio)-4-(4'hydroxyphenoxy)-phenylalanine, 3,5-di(ethylthio)-4(3'-isopropyl-4'-methoxyphenoxy)-phenylalanine, β-pyrrolyl-alanine, 2-amino-4-pyrrolylbutyric acid, 2-amino-5-pyrrolyl-valeric acid, β-(2 pyridyl)alanine, β-(3 pyridyl)alanine, β-(6-aminopurin-9yl-)alanine, β-(4-amino-2-hydroxy-pyrimidin-1-yl)alanine, β-(2,4 dihydroxy-5 methyl-pyrimidin-1-yl)alanine, β-(6-hydroxy-purin-9-yl)alanine, β(6-dimethylamino-purin-9-yl)alanine, β-(6-mercaptopurin-9-yl)alanine, β-(6-methylthiopurin-9-yl)alanine, 4-azatryptophan, 4-methyl-6-chloro-7-azatryptophan, $N^{\epsilon}$-(1,4-dehydro-6 methyl-3-hydroxy-4-oxo-1-pyridyl)lysine, S-(2-hydroxy-2-carboxyethanethiomethyl)-cysteine, 2-amino-3-(6-thieno[3,2-b]pyrrolyl)propionic acid, 3,3',5,5' tetramethyl thyronine, 3-hydroxy-L-lysine, 2-aminohex-4-ynoic acid, N-hydroxyornithine, 4-piperazinobut-2-ynoic acid, 4-piperidinobut-2-ynoic acid, 4-pyrrolidinobut-2-ynoic acid, α-amino-$N^{\gamma}$-nitroguanidinobutyric acid, α-aminoβ(1-imidazolyl)-propionic acid, 4-nitrohistidine, 2-methyl-3(2',4'-diiodo 5'-hydroxyphenyl)alanine, 4-(3'amino-2',4',6'-triiodophenyl)-isovaline, 4-(3' acetamido-2',4',6'-triiodophenyl)-isovaline, 4-(3'-hydroxy-2',4',6'-triiodophenyl-)isovaline, 2-amino-4-thiosulfobutyric acid, S-(3-aminopropyl)homecysteine, S-(cyclopentyl methyl)homocysteine, 5'-guanosyl homocysteine, β(cytosin-1-yl)-alanine, S-[(diphenyl-α-naphthyl)methyl]-L-cysteine, S-[(diphenyl-β-naphthyl)methyl]-L-cysteine, 2-amino-6-(methylthio)caproic acid, $N^{G}N^{G}$-dimethyl-L-arginine, $N^{G}N'^{G}$-dimethyl-L-arginine, $N^{\epsilon}N^{\epsilon}N^{\epsilon}$-trimethyl-δ-hydroxy-L-lysine, $N^{\epsilon}$-(5-amino-5-carboxypentyl)-5-hydroxy-L-lysine, $\delta^{\epsilon}$-dihydroxy-L-norleucine, cis-1-amino-1,3-dicarboxycyclohexane, trans-1-amino-1,3-dicarboxycyclohexane, 3,3,4,4,4,-pentafluoro-2-aminobutyric acid, 3,3,4,4,5,5,5,-heptafluoro-2-aminovaleric acid, ω-fluoro-DL- and L-allo-isoleucine, 2,6-diamino-4-hexynoic acid, O-(α-D-glucopyranosyl)-L-serine, 2-amino-5,6-dihydroxyindan-2-carboxylic acid, 3-(m-fluorophenyl)-2-methylalanine, 3-(m-bromophenyl)-2-methylalanine, 3-(m-iodophenyl)-2-methylalanine, 2-[(m-iodophenyl)methyl]glycine, 4-(m-iodophenyl)-2-methyl-2-aminobutyric acid, 3,5,3'-tri-isopropyl-DL-thyronine, 3,5-dimethyl-3'-isopropyl-thyronine, 3,5-di-isopropyl-thyronine, 3,5-di-isopropyl-4'-amino-thyronine, 3,5-di-isopropyl-3'-bromo-thyronine, 3,5-di-isopropyl-3'-methyl-thyronine, 3,5-di-s-butyl-thyronine, 3,5-di-s-butyl-4'-amino-thyronine, 3,5-di-s-butyl-3'-bromo-thyronine, 3,5-di-s-butyl-3'-iodo-thyronine, 4-fluoro-tryptophan, 5-fluoro-tryptophan, 6-fluoro-tryptophan, β-5(-hydroxy-6-ioso-2-pyridyl)-alanine, β-(benzimidazol-5-yl)-alanine, β-(2-amino-6-hydroxypurin-9-yl)-alanine, β-(2-amino-6-mercaptopurin-9-yl)-alanine, $N^{\epsilon}$-(5-Amino-6-chloro-4-pyrimidyl)lysine, α-Amino-ε-(6-chloro-9-purinyl)caproic acid, 4-Fluoro-DL-histidine, S-Methyl-2-methyl-cysteine, S-Ethyl-2-methyl-cysteine S-Propyl-2-methyl-cysteine, S-Isopropyl-2-methyl-cysteine, S-Butyl-2-methyl-cysteine, S-Isobutyl-2-methyl-cysteine, S-t-Butyl-2-methyl-cysteine, S-Amyl-2-methyl-cysteine, S-Isoamyl-2-methyl-cysteine, S-Allyl-2-methyl-cysteine, S-(β-Aminoethyl)homocysteine, γ,δ,δ'-trihydroxy-leucine, $N^{\epsilon}$-(indole-3-acetyl)-lysine, p-hydroxymethylphenylalanine, O-ethylhomoserine, 5-methyl-2-aminohex-4-enoic acid, α-(3-hydroxyphenyl)glycine, α-(3,5-dihydroxyphenyl)glycine, β-(cyclohexa-1,4-dienyl)alanine, β-(cyclohex-1-enyl)-alanine, β-(1-hydroxycyclohexyl)-alanine 4-bromoacetyl-phenylalanine, 4-bromoacetamido-phenylalanine, 3-chloroacetamido-phenylalanine, 4-fluoro-3-chloroacetamido-phenylalanine, 3,4,5-tri-iodo-phenylalanine, 3,5-di-isopropyl-3'-iodo-thyronine, β-(4-methoxy-1-naphthyl)-α-methylalanine, β-(4-hydroxy-1-naphthyl)-α-methylalanine, α-(2-indanyl)glycine, β-trimethylsilyl-alanine, α-amino-β-(methylamino)propionic acid, $N^{\epsilon}N^{\epsilon}$-bis(2-cyanoethyl)-lysine, α,γ-dimethylnorleucine, α-methyl-$N^{\epsilon}N^{\epsilon}$-diethylornithine, α-ethyl-3,4-dimethoxy-phenylalanine, α-methyl-4-morpholino-phenylalanine, β-(2-amino-4-pyrimidinyl)alanine, 3-(2-Methyl-4,5-dihydroxyphenyl)-alanine, 3-(2-Ethyl-4,5-dihydroxyphenyl)-alanine, 3-(2-Isopropyl-4,5-dihydroxyphenyl)-alanine, 3-(2-t-Butyl-4,5-dihydroxyphenyl)-alanine, 3-(2,5-Dimethoxy-4-methylphenyl)-alanine, 3-Ethyl-α-methyl-tyrosine, 2-amino-3,3-dimethylhex-5-enoic acid, 2-aminohexa-4,5-dienoic acid, 2-amino-3,3-dimethylhexa-4,5-dienoic acid, 2-aminohepta-4-5-dienoic acid, 2-amino-3,3-dimethylhepta-4,5-dienoic acid, 2-amino-3,3-dimethylnona-4,5-dienoic acid, 2-aminohepta-5,6-dienoic acid, 2-amino-3-methylhepta-5,6-dienoic acid, 2-amino-5-t-butyl-6,6-dimethylhepta-3,4-dienoic acid, 2-amino-5-methylhepta-3,4-dienoic acid, 2-aminohept-4-en-6-ynoic acid, ε-hydroxy-β-carboxy-norleucine, β-carboxy-lysine, β-(3,4-dihydroxyphenyl)-α-methyl-serine, S-benzyl-β,γ-dimethyl-homocysteine, S-benzyl-α,γ,γ-trimethyl-homocysteine, β-methyl-methionine, α-methyl-selenomethionine, β-methyl-L-selenomethionine, γ-methyl-selenomethionine, γ,γ'-difluoro-valine, δ,δ'-difluoro-leucine, γ-fluoro-allothreonine, β-hydroxy-asparagine, β-hydroxy-isoleucine, β-methoxy-isoleucine, αamino-γ-(methylamino)butyric acid, α-amino-β-(ethylamino)propionic acid, 3-Isopropyl-α-methyl-tyrosine, 3-t-Butyl-α-methyl-tyrosine, 2-Amino-5-hydroxy-indan-2-carboxylic acid, 2-Amino-5-methoxy-indan-2-carboxylic acid, 2-Amino-5-carboxy-indan-2-carboxylic acid, 2-Amino-5-chloro-indan-2-carboxylic acid, 2-Amino-5-bromo-indan-2-carboxylic acid, 2-Amino-5-iodo-indan-2-carboxylic acid, 3-(2,4-Difluorophenyl)-alanine, 3-(3,4-Difluorophenyl)-alanine, 3-(3,5-Difluorophenyl)-alanine, 3-(2,5-Difluorophenyl)-alanine, 3-(2,6-Difluorophenyl)-alanine, 3-(2,3,5,6-Tetrafluorophenyl)-alanine, 3-(3,5-Dichloro-2,4,6-trifluorophenyl)-alanine, 3-(2,3,4,5,6-Pentafluorophenyl)-alanine, β-(1,2-Dihydro-2-oxo-3-pyridyl)-alanine, β-(1,2-Dihydro-2-oxo-4-pyridyl)-alanine, β-(1,2-Dihydro-2-oxo-5-pyridyl)-alanine, β-(1,2-Dihydro-2-oxo-6-pyridyl)-alanine, β-(2-Fluoro-3-pyridyl)-alanine, β-(2-Fluoro-5-pyridyl)-alanine, β-(2-Fluoro-6-pyridyl)-alanine, β-(2-Bromo-3-pyridyl)-alanine, β-(2-Bromo-4-pyridyl)-alanine, β-(2-Bromo-5-pyridyl)-alanine, β-(2-Bromo-6-pyridyl)-alanine, β-(2-Chloro-3-pyridyl)-alanine, β-(2-Chloro-4-pyridyl)-alanine, β-(2-Chloro-5-pyridyl)-alanine, β-(2-Chloro-6-pyridyl)-alanine, β-(Thymin-1-yl)-alanine.

It is further contemplated that

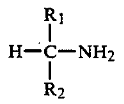

may be selected from among any of the known amino acids or esters or from amides thereof in which, $R_1$ is any of $CH_3$, $NH_2—(CH_2)_3$, $NH_2(CH_2)_4—$, $CH_3S(CH_2)_2—$, benzyl—, p-hydroxybenzyl, 3,4-dimethoxybenzyl,

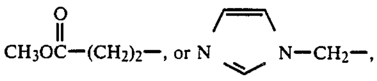

It is also contemplated that reactants of the general formula

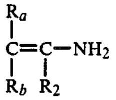

wherein $R_2$ is COOH may be utilized in lieu of

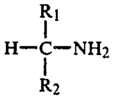

in the coupling reaction with

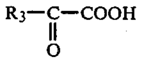

or its coupling product already described. In such case,

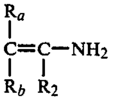

may be, e.g., dehydroalanine, α,β-dehydrophenylalanine, vinyl glycine or a known compound in which $R_a$ and $R_b$ are both methyl or ethyl or $R_a$ is a phenyl or a substituted phenyl group such as 3,4 dimethoxyphenyl and $R_b$ is methyl. In this instance various functional groups such as halo, hydroxy or mercapto groups and their methylene analogs, may later be added to one or both carbons of the unsaturated bonds via well known and conventional organic chemical procedures.

Many suitable variations in

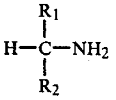

will readily occur to those of ordinary skill in the art.

Another general method for synthesizing compounds of this invention is to couple a suitable α keto carboxylic acid with a suitable dipeptide derivative. A suitable α keto acid can be formed in the reaction,

I

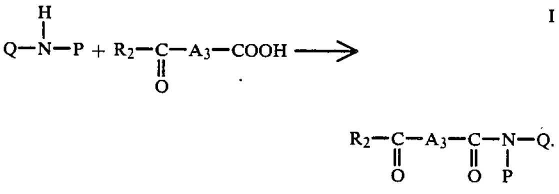

in the presence of a conventional coupling agent. An appropriate dipeptide derivative can be formed in the reaction

II

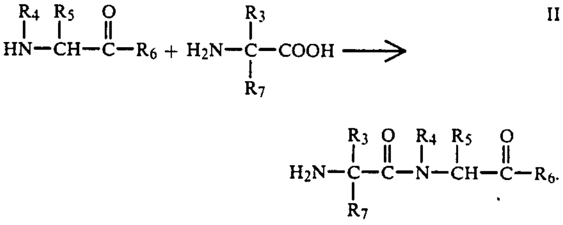

Compounds of this invention are then obtained by reacting I and II. Alternative schemes are readily apparent, for example,

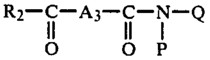

may be reacted with

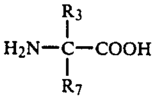

and the product then reacted with

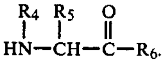

Suitable compounds of the formula,

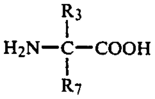

include, but are by no means limited to 2-methylalanine, histidine, N-acetyl-lysine, tryptophan, α-methyltryptophan, albizziin, 2-amino-adipic acid, p-amino-phenylalanine, phenylalanine, arginine, aspartic acid, asparagine, 2-methylglutamic acid, N-hydroxylysine, 2-amino-3-adamantyl propionic acid, α-hydroxymethylalanine, α-methyl methionine, α-Methyl-N,N-diethylornithine, α-methyl-4 morpholino-phenylalanine, β-(4-methoxy-1-naphthyl) α-methylalanine, and β-(4-hydroxy-1-naphthyl)α-methylalanine, α-ethyl-3,4-dimethoxy phenylalanine and others which will readily occur to those of ordinary skill in the art.

So long as $R_1$ is of the formula

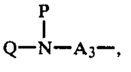

any compound of the general formula

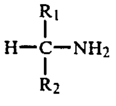

given above, wherein $R_2$=COOH may be used as

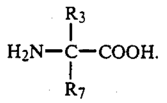

In these cases, $R_1$ becomes $R_3$, and $R_7$ becomes H.

Useful compounds of the type

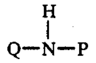

include aminoacenaphthene, para-morpholinoaniline, piperidine, phenylpiperidine, hydantoin, alloxazine, rhodamine, morpholine, aminophenanthrene, adenosine, adamantanamine, adenine, C-aminoacridine, C-aminopyrimidine, aminoanthracene, aminoanthraquinone, aminoantipyrine, aminophenol, aminonaphthalene, aminobenzophenone, C-aminobenzothiadiazole, C-aminobenzothiazole, benzothiazole, aminobiphenyl, C-aminopyridine, C-aminothiazole, pyrazole, C-aminopyrazole, C-aminobenzoxazole, C-aminpurine, aminochrysene, aminocyclopentane, aminocylcopropane, aminocyclobutane, aminocyclohexane, aminocycloheptane, aminocyclooctane, aminocyclononane, aminocyclodecane, C-amino-benzimidazole, C-aminopteridine, N-aminopiperidine, C-amino-1,2,4-triazine, C-aminouracil, uracil, C-amino,N,N-dimethyluracil, aminodiphenylmethane, N-aminoethylimidazolone, N-aminoethyl-morpholine, C-aminomorpholine, N-aminoethylpiperazine, C-aminopiperazine, N-aminoethylpiperidine, 3-amino-N-ethyl-piperidine, 2-aminoethylpyridine, N(aminoethyl)-pyrrolidine, pyrrolidine, aminofluoroanthene, 1-, 2-, or 4-aminofluorenone, aminohexane, aminopentane, N-aminohomopiperidine, homopiperidine, 1-amino,4-(βhydroxyethyl)piperazine, amino-9-hydroxyfluorene, 2-amino-4-hydroxy-6-methylpyrimidine, 4-amino-6-hydroxypyrazole, 4-aminoimidazole, aminoindan, C-aminoindazole, C-aminoindole, 1- or 5-aminoisoquinoline, 3-amino-mercapto-1,2,4-triazole, 4-aminobutanol-1,5-amino-pentanol-1,2-aminomethyl-1-ethylpyrrolidine, 5-aminoisothiazole, 2-amino-6-methylmercaptopurine, 6-aminohexanol-1,1-amino-4-methylpiperazine, 4-aminomethylpiperidine, 2-amino-1,3,4-thiadiazole, 2-amino-4-methyl thiazole, N-aminomorpholine, 2-amino-4-morpholine-s-triazine, 4-amino-1,8-naphthalimide, 6-aminonicotinamide, 5-amino-6-nitroquinoline, 2-amino-5-nitrothiazole, 6-aminopenicillanic acid, 4-aminophenyl ether, 2(p-aminophenyl)-6-methylbenzothiazole, 3-amino-1-phenyl-2-pyrazolin-5-one, 3-aminophthalhydrazide, N-aminophthalimide, 2-aminopecoline, N-aminopiperidine, 3-aminopropanol1, N-(3 aminopropyl)morpholine, N-(3 aminopropyl), ethanolamine, N(3-aminopropyl)pyrrolidinone, 2-amino-6 purinethiol, aminopyrazine, 3-aminopyrazole, 4-aminopyrazolo-pyrimidine, aminopyrene, 4-aminoquinaldine, N-aminorhodanine, 4- or 5-aminosalicylic acid, 5-aminotetrazole, tetrazole, 2-aminothiazoline, aminovaleric acid, aniline, 3,4-dimethoxyaniline, aminoxylene, benzisooxazole, o- or p-aminobenzamide, o- or p-aminobenzoic acid, o- or p-aminobenzonitrile, 8-aza-6-aminopurine, 2-azacyclooctanone, 3-azabicyclononane, 2-azacytidine, 5-azacytosine, cytosine, 6-azacytosine, 5- or 6-azauracid, azetidine, aminoazulene, barbituric acid, aminobenzofluorene, C-aminobenzofuran, benzothiazinone, benzylpiperazine, bis(2-ethoxyethyl)amine, bromoguanine, bromoisatin, ε-caprolactam, carbazole, tryptophan, glycine, glycinamide, glycinanilide, oxazolidine, oxazolidinone, 8-chlorotheophylline, chlorooxazone, creatinine, aminocycloheptadiene, aminocyclooctatriene, aminocyclooctratetraene, cycloserine, cytidine, cytosinecarboxylic acid, dehydroabietylamine, 4,5-diaminoacetanaphthene, aminobenzidine, aminothiophene, dimethylhydantoin, aminofuran, N,N-diethylethylenediamine, aminotoluene, aminoindenone, ethyl-4-amino-5-imidazole carboxylate, α-methyltryptamine, glutamine, glutathione, glutarimide, guanine, guanosine, histamine, dodecamethyleneimine, homocarnosine, dithiouracil, 2,2'-dipyridylamine, 2,5-dimethyl-3-pyrroline, 2,6-dimethylpiperazine, isoamarine, glycoluril, leucinol, leucenol, myrtanylamine, nicotinamide, homopiperazine, isonicotinamide, 6-β-hydroxyethylamino purine, aminonorbornane, aminonorborene, orotic acid, oxindole, phenoxazine, proline, phthalimide, pyrimidone, pyrole, <Glu, thiazolidine, triacanthine, and 1,2,4-triazole. The various compounds named can be substituted with, e.g., —OH, halo, dihalomethy, trihalomethyl, —SH, O-alkyl, S-alkyl, phenyl, O-phenyl, S-phenyl, COOY, alkylcarbonyloxy, ureido, cyano, hydroxylamino, alkyl, alkoxyalkyl, alkoxyphenyl, phenoxyphenyl and the like. These compounds are illustrative, rather than limiting, as to suitable

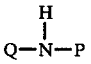

compounds.

It will be understood that

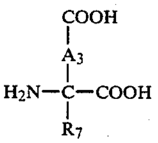

may be utilized in this particular scheme and the $A_3$-COOH converted to

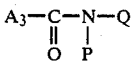

at any desired stage of the synthesis process.

A variety of known methods can be employed to esterify or block any carboxyl group of a multi-carboxyl amino acid or and α-keto carboxylic acid. See, for example, Schroder E. et al., The Peptides Vol. 1, Academic Press (1965) pp. 181–207, and Merrifield, R. B., *Adv. Enzym* 32, 221 (1969). Furthermore, many of these precursors can be obtained commercially, e.g., from Chemical Dynamics, South Plainfield, N.J., or from Bachem Chemical Co., Torrance, Calif.

Another method for synthesizing compounds of Formula I involves the use of a diazomethyl intermediate. See, for example, Boyer, J. H. et al., *Chem. Rev.* 54, 1-57 (1954); *Aldrichimica Acta,* 3(4), 9 (1970) an article available from Aldrich Chemical Co., Milwaukee, Wis.; Lieber, E. et al., *Chem. Rev.* 65, 377-384 (1965); L'Abbe, G. *Chem. Rev.* 69, 345-363 (1969). This method is especially useful for synthesizing compounds of the invention wherein $A_3$=—$CH_2$—. Typically a carboxylic acid is reacted with diazomethane via a mixed anhydride reaction, e.g.,

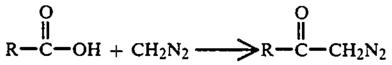

the product is then reacted with an acid such as HBr or HCl, in a solvent such as ethyl acetate, to form an α-haloketone as follows:

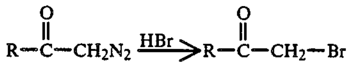

The α-haloketone can then be reacted with an equivalent of diethylformamidomalonate, than decarboxylated in aqueous HCl to form derivatives of 2-amino-4-keto carboxylic acid, that is compounds of the formula

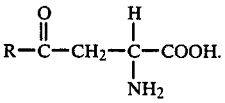

Compounds of this general formula can then be coupled with compounds of general formula

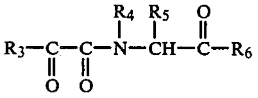

in the presence of a reducing agent such as sodium cyanoborohydride in aqueous solution with an organic solvent (for example $CH_2Cl_2$ or $CHCl_3$) to form compounds of the invention. Alternatively,

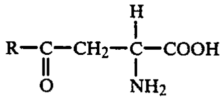

can be coupled with

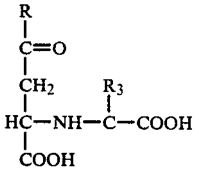

which in turn is coupled with

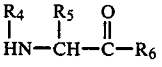

in the presence of DCC or DPPA to form a compound of this invention.

The diazomethyl intermediate can be formed with virtually any carboxylated organic compound. Thus,

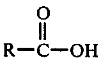

can be a difunctional or trifunctional amino acid, any dicarboxylic acid or any carboxylic acid. Appropriate protecting groups may also be necessary.

The secondary amine compounds of this invention can also be synthesized by the following method. The compound

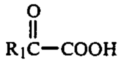

is coupled with thiophenol using the mixed anhydride method to produce

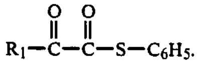

This product is then reacted with

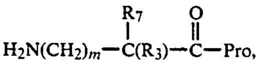 to yield

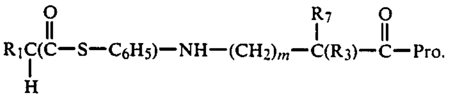

This compound is reacted with NaSH to form

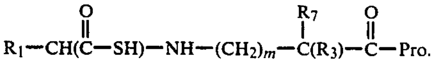

Compounds of this invention in which $R_1$ and $R_2$ are bridged to form a lactone ring can be prepared using 2-halolactones, e.g., α-Br γ-valerolactone and α-Br-γ-butyrolactone. The α-bromo group is reactive with

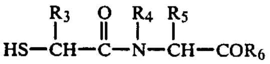

or those analogs in which an $NH_2$- or OH-group is substituted for the HS-group to form compounds of this invention. ΔPro cannot be used in this procedure unless added as

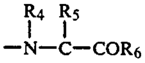

as a final step, i.e., after the

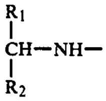

bond has been formed. The lactone ring can be opened, e.g., with a base such as $Ba(OH)_2$ to form the corresponding γ-OH-1-carboxymethyl compounds. The hydroxy-group can be converted to a salt with sodium, potassium or an organic cation such as that from arginine, or can be converted to an ethyl or methyl ether.

Compounds

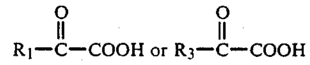

used in any of the procedures disclosed herein may be selected from known ketocarboxylic acids, including, but not limited to, pyruvic acid, phenylpyruvic acid, 3-cyclohexyl-2-oxopropionic acid, 6-methyl-2-oxoheptanoic acid, 4-methyl-2-oxopentanoic acid, 2-oxobutyric acid, 3-methyl-2-oxobutyric acid, 2-oxoglutaric acid, 2-oxoadipic acid, 2-oxo-4-phenylbutyric acid, 4-(3-indolyl)-2-oxobutyric acid, N-acetylaminoethyl-2-oxo-4-phenylbutyrate, dimethylaminoethyl-2-oxo-4-phenylbutyrate, 2-oxo-5-methylhexanate, phenoxypyruvic acid, phenylthiopyruvic acid, 4-p-chlorophenyl-2-oxobutyrate, indole-3-pyruvic acid, 2-oxo-3-p-cyanophenylpropionate, 4-α-naphthyl-2-oxobutyrate, 4-(3,4-dichlorophenyl)-2-oxo-butyrate), or 2-oxo-4-p-phenoxyphenylbutyric acid.

The compounds of this invention have one or more asymmetric carbons as indicated by the asterisks in the general formula. The compounds accordingly exist in stereoisomeric forms or in racemic mixtures thereof. All of these are within the scope of the invention. The above described syntheses can utilize a racemate or one of the enantiomers as starting material. When the racemic starting material is used in the synthetic procedure or a racemic mixture results from the synthesis, the stereoisomers obtained in the product can be separated by conventional chromatographic or fractional crystallization methods. In general, the S-isomer with respect to the carbon bearing $R_1$ constitutes the preferred isomeric form. Also the S-isomer of the carbon bearing $R_5$ is preferred.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic basis, e.g., dicyclohexylamine, benzathine, N-methyl-D-glucamine, procaine salts, and salts with amino acids like arginine, lysine, and the like. The non-toxic, physiologically acceptable salts are preferred.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance with has been implicated as the causative agent in various forms of hypertension in various mammalian species, e.g., rats and dogs. The compounds of this invention intervene in the $$\text{angiotensin} \xrightarrow{\text{(renin)}} \text{angiotensin I} \xrightarrow{\text{(ACE)}}$$

angiotensin II sequence by inhibiting angiotensin converting enzyme and reducing or eliminating the formation of the pressor substance angiotensin II. Thus by the administration of a composition containing one or a combination of compounds of formula I including their physiologically acceptable salts, angiotensin-dependent hypertension in the species of mammal suffering therefrom is alleviated. A single dose, or in some cases up to two to four divided daily doses, provided on a basis of about 0.03 to 20 mg per kilogram per day, is appropriate to reduce blood pressure. The substance is preferably administered orally, but parenteral routes such as subcutaneous, intramuscular, intravenous or intraperitoneal can also be employed.

The compounds of this invention can be utilized to achieve the reduction of blood pressure by formulating them in compositions such as tablets, capsules or elixirs for oral administration or in sterile solutions or suspensions for parenteral administration. About 10 to 500 mg of a compound of mixture of compounds of formula I, including the physiologically acceptable salts thereof, is compounded with a physiologically acceptable vehicle, carrier, excipient, binder preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, gum acacia, corn starch or gelatin; an exipient such as dicalcium phosphate; a disintegrating agent such as corn starch, potato starch, alginic acid and the like; a lubricant such as magnesium stearate; a sweetening agent such as sucrose, lactose or saccharin; and a flavoring agent such as peppermint, oil of wintergreen or cherry. When the dosage unit form is a capsule, it may contain in addition to materials of the above type a liquid carrier such as a fatty oil.

Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye, and a flavoring such as cherry or orange flavor. Antioxidants may also be added. Suitable antioxidants are α-tocopherol nicotinate, vitamin A, C, E and analogs of vitamin E known in the art, retinal palmitate and otheer antioxidants known in the art as food additives such as the gallates.

Sterile compositions for injection can be formulated according to conventional pharmaceutical practice by dissolving or suspending the active substance in a vehicle such as water, a naturally occurring vegetable oil like sesame oil, coconut oil, peanut oil, cottonseed oil, etc., or a synthetic fatty vehicle like ethyl oleate or the like. Buffers, preservatives, and the like can be incorporated as required.

The present invention will be further described by the following examples. All temperatures are in degrees Celsius unless otherwise indicated. Molar equivalents of the reactants are usually utilized.

EXAMPLE 1

Synthesis of N-(L-1-carboxy-2-propylaminocarbonylethyl)-D,L-Ala-L-Pro

A. 200 mmoles of propylamine and 150 mmoles of the -ethyl ester of N-Boc aspartic acid are dissolved in 600 ml of cold dimethylformamide (DMF) and 125 mmoles of DPPA. A volume of 25 ml of triethylamine in DMF is added drop-wise, holding the temperature at about −10° C. for two hours. The reaction is stored overnight at room temperature and rotary evaporated to remove DMF. The product is 3-(propylamino-carbonyl)-2-aminopropanoic acid ethyl ester. The Boc group is removed with TFA.

B. A solution of 60 mmoles of pyruvic acid plus 60 mmoles of L-proline ethyl ester in redistilled chloroform is cooled to −50° C. in an acetone-dry ice bath. To this solution is added 60 mmoles of a precooled solution of dicyclohexylcarbodiimide (DCC) in cloroform and the mixture is stirred at −5° C. for 1 hour. The reaction mixture is slowly warmed to room temperature and stirred for an additional 2 hours and then stirred at 4° C. overnight. The mixture is filtered to remove dicyclohexylurea, then cooled in an ice bath. The organic phase is washed with cold water, cold 1N $NaHCO_3$ and finally with cold saturated NaCl. The organic phase is dried over anhydrous $MgSO_4$ and filtered. The solvent is removed with a rotary evaporator yielding N-pyruvoyl-L-proline ethyl ester.

C. 40 mmoles of the product of Step A is reacted with 200 mmoles of the product of Step B in ethanol with stirring in the presence of molecular sieves at room temperature. A solution of 40 mmoles of sodium cyanoborohydride in ethanol is then slowly added over the course of 6 hours. The reaction mixture is filtered and the solvent removed by a rotary evaporator. The product is purified by partition chromatography (Sephadex G-25), developed with butanol/acetic acid/$H_2O$ (4:1:5). The ethyl esters are removed by saponification to yield the named product.

EXAMPLES 2-15

By substituting any one of the reactants for propylamine of Example 1, and following the procedures of Example 1, compounds are obtained with $R_1$ groups as shown in the Table.

TABLE

| Example | Reactant | $R_1$ |
|---|---|---|
| 2 | butylamine | 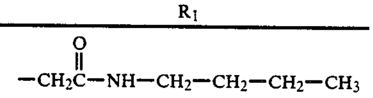 |
| 3 | cyclopentyl-amine | 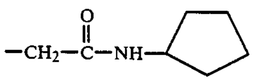 |

TABLE-continued

| Example | Reactant | $R_1$ |
|---|---|---|
| 4 | L-proline | 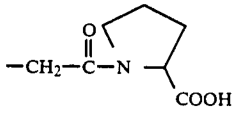 |
| 5 | adenine | 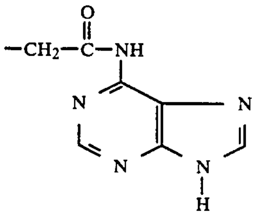 |
| 6 | indoline | 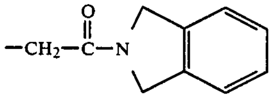 |
| 7 | 2-azacyclo-octanone | 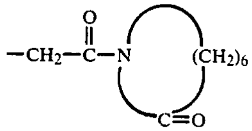 |
| 8 | aniline | 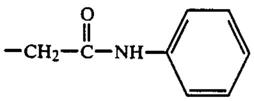 |
| 9 | 2-amino-5-bromopyridine | 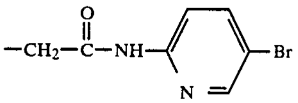 |
| 10 | 2-amino-5-chlorothiazole | 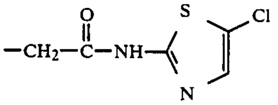 |
| 11 | N—amino piperidine | 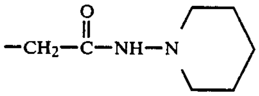 |
| 12 | isobutyramide | 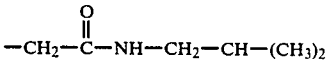 |
| 13 | maleimide | 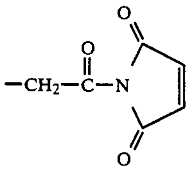 |
| 14 | diacetamide | 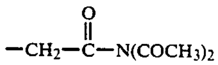 |
| 15 | diallylamine | 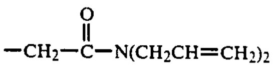 |

EXAMPLE 16

Synthesis of N-[1-carbethoxy-3-(methylaminocarbonyl)propyl]-L-Ala-L-Pro

A solution of 50 mmoles of 4-methylaminocarbonyl-2-oxobutyric acid ethyl ester and 10 mmoles of L-Ala-L-Pro butyl ester in ethanol is stirred with powdered molecular sieves at room temperature for 30 minutes. A solution of sodium cyanoborohydride, 10 mmoles, in ethanol is added slowly over the next 5 hours. The mixture is filtered, and the solvent of the filtrate is removed with a rotary evaporator and the t-butyl ester is removed by treatment with TFA. The product, N-[1-carbethoxy-3-methylaminocarbonyl)butyl]-alanylproline, is obtained after partition column chromatography [butanol/acetic acid/$H_2O$ (4:1:5 by vol.)].

EXAMPLE 17

Synthesis of N-[(1-carboxy-3-carboanilide)propyl]-δ-propylamido-L-glutamyl-L-pro A. 175 mmoles of propylamine and 150 mmoles of the α-ethyl ester of Boc-glutamic acid are dissolved in 600 ml of DMF and 125 mmoles of DPPA. A volume of 25 ml of triethylamine is added drop-wise, holding the temperature at about −10° C. for 2.5 hours. The reaction is stored overnight at room temperature, rotary evaporated to remove DMF, then the product γ-propylamido-L-Boc-glutamic acid ethyl ester, is saponified and then purified by chromatography on silica gel.

B. 100 mmoles of the product is then reacted with 100 mmoles of L-proline-t-butyl ester in redistilled dichloromethane, precooled to −5° C. To this solution is added 100 mmoles of a precooled solution of dicyclohexylcarbodiimide in dichloromethane and the mixture is stirred in an ice bath for 2 hours. The reaction mixture is slowly warmed to room temperature and then stirred at 4° C. overnight. The mixture is filtered to remove dicyclohexylurea, then cooled in an ice bath. The organic phase is washed with cold 1N HCl, cold 1N $NaHCO_3$ and finally with cold saturated NaCl. The organic phase is dried over anhydrous $MgSO_4$ and filtered. The solvent is removed with a rotary evaporator yielding γ-propylamido-Boc-L-glutamyl-L-pro-t-butyl ester. The t-butyl ester and Boc group are removed with TFA.

C. A solution of 50 mmoles of the glutamic acid analog of the product of Synthesis A of Example 8 and 250 mmoles of 4-anilinocarbonyl-2-oxo-butyricacid t-butylester in ethanol is stirred with powdered molecular sieves at room temperature for ½ hour. A solution of 50 mmoles sodium cyanoborohydride in ethanol plus 300 mmoles of $NaHCO_3$ in water is slowly added over the course of six hours. The reaction is filtered. The t-butyl esters are removed by treatment with trifluoroacetic acid in anisole. The named product is obtained after removal of the solvent with a rotary evaporator.

EXAMPLES 18–24

Synthesis A of Example 17 is followed, substituting propylamine and the 1-ethylester of Boc-glutamic acid with each pair of reactant compounds in the following Table. The product is then reacted with L-proline-tert-butyl ester according to Synthesis B of Example 17. A solution of 10 mmoles of the product and 50 mmoles of 4-carboanilide-2-ketobutyric acid ethyl ester in ethanol is stirred with powdered molecular sieves at room temperature for ½ hour. A solution of 40 mmoles of sodium cyanoborohydride in ethanol is slowly added over the course of six hours. The reaction mixture is filtered and the t-butyl ester is removed by treatment with trifluoroacetic acid in anisole. The solvent is removed with a rotary evaporator. A series of analogs of the product of Example 17 are obtained, which products have $R_3$ and $R_7$ groups given in the Table.

TABLE

| Example | Pair of Reactants | $R_7$ | $R_3$ |
|---|---|---|---|
| 18 | methylamine, 1-ethyl ester of Boc—glutamic acid | H | 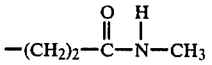 |
| 19 | methylamine, 1-ethyl ester of Boc—2-amino-malonic acid | H | 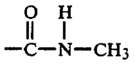 |
| 20 | methylamine, 1-ethyl ester of Boc—aspartic acid | H | 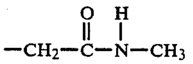 |
| 21 | aniline, 1-ethyl ester of Boc—2-amino-adipic acid | H | 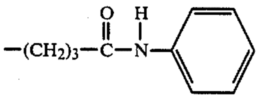 |
| 22 | aniline, 1-ethyl ester of $N^{\alpha}$—Boc—p-carboxy-phenylglycine | H | 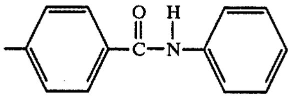 |
| 23 | propylamine, 1-ethyl ester of $N^{\alpha}$—Boc—p-carboxy-phenylalanine | H | 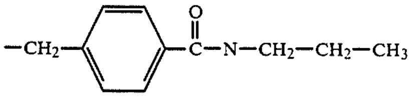 |

TABLE-continued

| Example | Pair of Reactants | $R_7$ | $R_3$ |
|---|---|---|---|
| 24 | aniline, 1-ethyl ester of $N^{\alpha}$—Boc—α-methyl aspartic acid | $-CH_3$ | 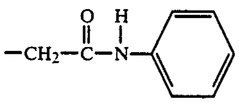 |

EXAMPLE 25

Preparation of N-[L-1-benzyloxycarbonyl-3-(carbo-4-iodoanilide)-propyl]-Alanyl-L-Proline

A. Synthesis of L-glutamic acid-α-benzyl ester-γ-4-iodoanilide

A solution of 4 mmoles of Nα-Boc-L-Glu-γ-2-$NO_2$-phenyl ester-α-benzyl ester in 3 ml of $CH_2Cl_2$ was added to a solution of 4.1 mmoles of 4-iodo-aniline in 3 ml of $CH_2Cl_2$ and the resulting solution was stirred at room temperature overnight. (The reaction was judged to be complete by thin layer chromatography). An oily residue was obtained after work-up. The product was dissolved in 4 ml of anhydrous trifluoroacetic acid. After 45 minutes at room temperature, the solvent was removed by rotary evaporation at 40° C. White crystals were formed after the addition of 4.5M HCl in ethyl acetate. The mixture was left at 0° C. for one hour and was filtered. The precipitate was washed with cold ethyl acetate in ether and then dried over $P_2O_5$ and NaOH in a vacuum desiccator. Yield 0.79 g; d.p. 119°-120° C.; second crop yield 1.11 g; d.p. 119°-120.5° C. The material was recrystallized from $CHCl_3$/isopropyl ether; d.p. 119.5°-120.5° C. Elemental analysis for $C_{18}H_{10}N_2ICIO_3$: Calculated C 45.54; H 4.24; N 5.90; I 26.73; Cl 7.47; O 10.11. Found: C 45.55; H 4.19; N 5.92; I 26.53; Cl 7.34.

B. Synthesis of N-[L-1-benzyloxycarbonyl-3-(carbo-4-iodoanilide)-propyl]-Ala-L-Pro-t-butyl ester A solution of the product of A (1 mmole in 1 ml of ethanol) was added with stirring to 1 mmole of $NaHCO_3$ in 0.2 ml of $H_2O$. To the resulting solution was added 5 mmoles of N-pyruvoyl-L-proline-t-butyl ester in 2 ml of ethanol plus 1.6 g of molecular sieves. The mixtures was stirred for 30 minutes at room temperature. Sodium cyanoborohydride, 65 mg in 1.5 ml of ethanol, was added, drip-wise, over a period of 4 hours. The reaction mixture was left at room temperature overnight. The mixture was filtered, the filtrate saved, and the precipitate was washed several times with ethanol. Solvent of the combined filtrates was removed by rotary evaporation at 30° C. to yield a yellow oil. The crude product was purified on Sephadex LH-20 (2.22×99 cm column) developed with THF/isopropanol (3:7 by vol); 250 drops (5.8 ml/fraction). Fractions 33-35 contained the desired product.

C. The named compound of this Example was obtained by dissolving the desired product of B in 2 ml of anhydrous TFA. The solution was allowed to stand at room temperature for 30 minutes and then the trifluoroacetic acid was removed by rotary evaporation at 30° C. The residue was dissolved in a small amount of ethanol, and the solution was applied to a column (1.2×43 cm) of AG1-X2 ($OH^-$ form) in $H_2O$. The column was developed with $H_2O$, 62 ml, and then a linear gradient was developed between $H_2O$ and 0.5M ammonium acetate (2 liters total). The column was washed with 0.5M ammonium acetate (1 liter), 1.0M ammonium acetate (200 ml) and then with 1.0M ammonium acetate/ethanol (1:2 by vol). The desired product was eluted with the last-named solution. Solvent volume was reduced by rotary evaporation and then ammonium acetate ws removed by lyophilization and sublimation.

EXAMPLE 26

Preparation of N-[L-1-carboxy-3-(carbo-anilide)propyl]-Alanyl-L-Proline

The product of Example 25, 40 mg, in 3 ml of methanol, was reacted with 30 mg of 10% palladium on carbon and $H_2$ at 1 atmosphere for 3 hours at room temperature. The precipitate was removed by filtration, and the solvent of the filtrate was removed by rotary evaporation. The desired product was obtained by chromatography on Sephadex G-10 (1.2×96 cm column) developed and eluted with 2% pyridine in water (yield 12.1 mg).

EXAMPLE 27

Preparation of N-[L-1-carboxy-3-(carbo-4-iodo-anilide)propyl]-Alanyl-L-Proline The product of Example 25, 60 mg, was treated with 3 ml of anhydrous HF in the presence of anisole for 1 hr. The desired product was obtained by the chromatographic system of Example 26. Yield 22.15 mg.

EXAMPLE 28

Preparation of N-[L-1-carboxy-2-(carbopyrrolide)ethyl]-Alanyl-L-Proline

A. Synthesis of L-aspartic acid-βpyrrolide-αethyl ester

Nα-Cbo-L-aspartic acid-α-ethyl ester, 8 mmoles, in 5 ml of $CH_2Cl_2$ was cooled to −5° C. A cold solution of DCC, 8 mmoles in 3 ml of $CH_2Cl_2$ was added with stirring. To this solution was added 0.67 ml of pyrrolidine. Stirring was continued at −5° C. for 30 minutes and at 4° C. overnight. The mixture was filtered, and the precipitate was washed with ethyl acetate. The combined filtrate was washed until neutral. The organic phase was dried over $MgSO_4$ and then filtered. The solvent of the filtrate was removed under vacuum to yield 1.85 g of a yellow oil. The oil, 1.5 g, was dissolved in 20 ml of methanol and the Cbo-protecting group was removed by hydrogenolysis (150 mg of 10% palladium on carbon with $H_2$ at 10 pounds per square inch for 90 minutes). The mixture was filtered, and solvent was removed under vacuum to yield white crystals. Recrystallization was effected from methanol/isopropyl ether. The desired product remained in the mother liquid and was converted to its HCl salt by adding HCl in ethyl acetate. Solvent was removed and the residue was dried over $P_2O_5$ and KOH in a vacuum desiccator to yield a hydroscopic foam. Crystals, 0.47 g, were obtained from $CHCl_3$/ethyl acetate.

B. Alkylation of pyruvoyl-L-proline with the product of A (Example 28)

Molecular sieves (1.312 g) were added with stirring to a mixture of 0.206 g of hCl.L-Asp-β-pyrrolide-α-ethyl ester, 0.073 g of $NaHCO_3$ and 0.986 g of N-pyruvoyl-L-proline-t-butyl ester in 0.1 ml of $H_2O$ and 2.0 ml of ethanol at room temperature. The mixture was stirred for 30 minutes and then 0.054 g of sodium cyanoborohydride in 1.0 ml of ethanol was added drop-wise over a period of 4 hours. Stirring was continued for another 18 hours. The mixture was filtered and the precipitate was washed with ethanol. Solvent of the combined filtrates was removed by rotary evaporation to yield a yellow oil. The material was chromatographed on LH-20 (2.2×99 cm) and developed with THF/isopropanol (3:7 by vol). The residue obtained by rotary evaporation was dissolved in 1.2 ml of TFA. After 45 minutes at room temperature, TFA was removed and the material was purified by chromatography on AG1-X2 (1.2×38 cm) developed first with $H_2O$ and then with a linear gradient between $H_2O$ and 0.5M ammonium acetate. Apparently pure product, 31.5 mg, was obtained by chromatography on Sephadex G-10 (1.2×97 cm column) developed with 2% pyridine. The ethoxy group was removed by saponification.

EXAMPLE 29

In vitro assays of the potency of selected compounds as inhibitors of angiotensin converting enzyme Compounds of this invention were assayed through the following protocol: 25 microliters of buffer (0.05M Hepes buffer, pH 8.0, plus 0.1M NaCl and 0.75M $Na_2SO_4$) or 25 microliters of an inhibitor in buffer was added to the bottom of a 7 ml liquid scintillation vial. To this was added 100 microliters of buffered substrate [S], [$^3$H]benzoyl-Gly-His-Leu, 80 nM (25 Ci/mmole). The reaction was started by adding 100 microliters of partially-purified human plasma angiotensin converting enzyme, or 100 microliters of buffer alone. The concentration of enzyme [E] used was that required to hydrolyze 8–12% of substrate when incubated at 37° C. for 15 minutes. The scintillation vials and their contents were incubated at 37° C. for 15 minutes, and the reactions were stopped by adding 200 microliters of 0.5M HCl to each vial. The radioactive reaction product, [$^3$H]benzoyl-Gly(hippuric acid), was separated from unhydrolyzed substrate by adding and mixing (by inversion) 3 ml of Ventrex Cocktail No. 1 (Ventrex Laboratories, Inc., Portland, Maine), a fluid disclosed in copending U.S. patent application Ser. No. 184,653, filed Sept. 6, 1980. Extractable $^3$H was quantified by liquid scintillation counting. Substrate, in c.p.m., was quantified by scintillation counting of a vial containing 100 μl of buffered substrate in 5 ml of RIAfluor (New England Nuclear). The reaction mixture containing al constituents except for inhibitor was termed the control (C). The reaction mixture lacking enzyme and inhibitor was called the blank (B). Reaction mixtures containing inhibitor (varied over the range of $10^{-4}$–$10^{-12}$M) were called the test (T) reactions. Under the conditions of this assay, the reaction obeys first order enzyme kinetics, thus the concentration of inhibitor required to inhibit the rate of hydrolysis by half ($I_{50}$) approximates the Ki value. The results were estimated by use of the formula:

$$[E] = \frac{C - B}{[S]} \times 100 \times \frac{1}{15} \text{ min}$$

where C=control c.p.m.; B=blank c.p.m.; [S]=substrate c.p.m. The factor 100 converts fractional substrate utilization into percentage utilization, and 1/15 minute corrects to percentage substrate utilization/minute. Thus, [E] is enzyme activity in percentage substrate utilization/minute. By substituting T for C, hydrolysis rates are computed for the test reaction mixtures. By comparing a given test rate against the control rate, the degree of inhibition can be computed.

| Compound (Product of Example) | $I_{50}$ |
|---|---|
| 27 | $2.3 \times 10^{-10}$M |
| 26 | $5.2 \times 10^{-9}$M |
| 28 | $1.4 \times 10^{-7}$M |

EXAMPLE 30

Intravenous effectiveness of N-[L-1-carboxy-3-(carbo-4-iodoanilide)propyl]-D,L-Ala-L-Pro Rats (190–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 mg/kg of angiotensin I in 20 μl of 0.9 g % NaCl, an amount of angiotensin I sufficient to raise mean arterial blood pressure by approximately 48 mm Hg.

After the responsiveness of a given rat to angiotensin I was established, the named compound at 0.5 μmole/kg (drug dissolved in 15 microliters of 0.9% NaCl) was given intravenously. At time intervals, the effects of 400 ng/kg of angiotensin I on mean arterial blood pressure were tested. Results are shown below:

| Time After IV Administration (minutes) | Blood Pressure Response to 400 ng/kg of Angiotensin I (% of Control) |
|---|---|
| −5 | 100% (48 mm Hg.) |
| +1 | 33% |
| 5 | 42% |
| 10 | 46% |
| 15 | 52% |
| 20 | 60% |
| 25 | 67% |
| 30 | 71% |
| 35 | 71% |
| 50 | 83% |
| 60 | 92% |
| 70 | 100% |
| 80 min. | 104% |

EXAMPLE 31

Intravenous Effectiveness of N-[L-1-carboxy-3-(carboanilide)propyl]-Alanyl-L-Proline Experiments were carried out using rats according to Example 30. The results are shown below.

| Time After IV Administration (minutes) | Blood Pressure Response to 400 ng/kg of Angiotensin I (% of Control) |
|---|---|
| −5 | 100% (48 mm Hg.) |
| +1 | 42% |
| 5 | 37% |
| 10 | 37% |
| 15 | 40% |
| 20 | 40% |
| 25 | 40% |
| 30 | 35% |

-continued

| Time After IV Administration (minutes) | Blood Pressure Response to 400 ng/kg of Angiotensin I (% of Control) |
|---|---|
| 40 | 35% |
| 50 | 46% |
| 60 | 46% |
| 70 | 48% |
| 80 | 52% |
| 90 | 54% |
| 102 min. | 62.5% |

EXAMPLES 32-50

By substituting pyruvic acid in Synthesis B of Example 1 with any of the α-keto carboxylic acids (appropriately protected) in the following Table, and reacting the product with 3-(propyl amino-carbonyl)-2-amino-propanoic acid ethyl ester as in Synthesis A of Example 1, products with $R_3$ groups in the Table are formed.

TABLE

| Example | α-keto carboxylic acid | $R_3$ |
|---|---|---|
| 32 | pyruvic acid | $CH_3-$ |
| 33 | phenylpyruvic acid | 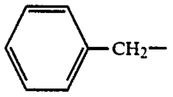 |
| 34 | 3-cyclohexyl-2-oxo-propionic acid | 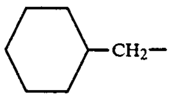 |
| 35 | 6-methyl-2-oxo-heptanoic acid | 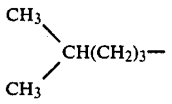 |
| 36 | 4-methyl-2-oxo-pentanoic acid | 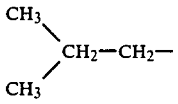 |
| 37 | 2-oxo-butyric acid | $CH_3-CH_2-$ |
| 38 | 3-methyl-2-oxo-butyric acid | 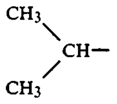 |
| 39 | 2-oxo-glutaric acid | $HOOC-CH_2-CH_2-$ |
| 40 | 2-oxo-adipic acid | $HOOC-CH_2-CH_2-CH_2-$ |
| 41 | 2-oxo-4-phenyl butyric acid | 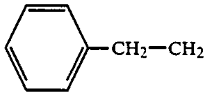 |
| 42 | 4-(3-indolyl)-2-oxo-butyric acid | 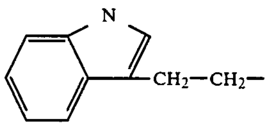 |
| 43 | phenoxypyruvic acid | 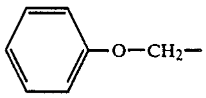 |

TABLE-continued

| Example | α-keto carboxylic acid | $R_3$ |
|---|---|---|
| 44 | phenylthio pyruvic acid | 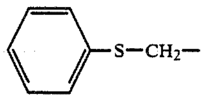 |
| 45 | 4-p-chlorophenyl-2-oxo-butyric acid | 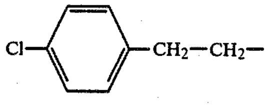 |
| 46 | indole-3-pyruvic acid | 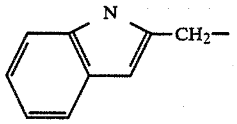 |
| 47 | 2-oxo-3-p-cyanophenyl-propionic acid | 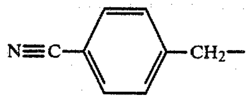 |
| 48 | 4-alpha-naphthyl-2-oxo-butyric acid | 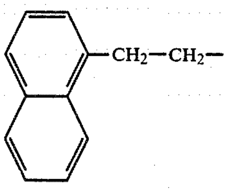 |
| 49 | 4-(3,4-dichlorophenyl)-2-oxo-butyric acid | 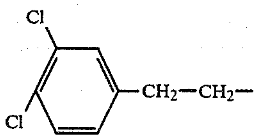 |
| 50 | 2-oxo-4-p-phenoxyphenyl butyric acid | 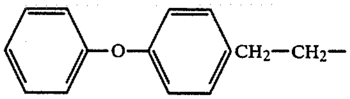 |

EXAMPLE 51

A. Synthesis of 2-keto-butyryl-L-<Glu

L-pyroglutamic acid (35 mmoles) is suspended in a mixture of 35 ml of propylene oxide and 210 ml of dry acetonitrile at room temperature. Bis-trimethylsilyl-trifluoro acetamide (77 mmole) is added and the reaction is stirred at room temperature for 15 minutes. 2-keto-butyric acid mixed carbonic anhydride (prepared by 2-keto-butyric acid, 36.8 mmole, triethylamine in isobutyl chloro formate) is added and the reaction is stirred at room temperature overnight. Acetonitrile is then removed in vacuo and the resulting residue is dissolved in ethyl acetate. The organic phase is washed with $H_2O$, then saturated NaCl, dried over anhydrous $Na_2SO_4$ and filtered, and the solvent removed with a rotary evaporator.

B. Synthesis of N-2-(1anilinocarbonyl-2-benzylthioethyl)butyryl-L-pyroglutamic acid Nα-Boc-S-benzyl-D-cysteine 100 mmoles is reacted with an equivalent of aniline in the presence of a slight excess of one equivalent of DCC (105 mmoles) by the method described in Synthesis B of Example 1. The Boc group is then removed with anhydrous TFA. 50 mmoles of the product is then coupled to 10 mmoles 2-keto-butyryl-L-<Glu (Synthesis A) with 10 mmoles of cyanoborohydride according to Example 16 to yield the named compound.

EXAMPLE 52

Synthesis of N-2(1-anilinocarbonyl-2-benzylthioethyl)propanoyl-L-pro

By substituting pyruvoyl-L-pro (Example 1) for 2-ketobutyryl-L-<Glu (Synthesis A of Example 51), and following the procedure of Synthesis B of Example 51, the named product is obtained.

EXAMPLE 53

Synthesis of N-[L-1-(N-acetylaminoethoxy carbonyl)-3-(carboanilide)propyl]-D,L-Ala-L-Pro-ethyl ester A solution of 50 mmoles of 2-Boc-amino-4-carboxy butyric acid N-acetyl aminoethyl ester is coupled to 50 mmoles of aniline in the presence of an equivalent of DCC according to Synthesis B of Example 1. The Boc group is then removed with anhydrous TFA. 40 mmoles of the product is then reacted with 200 mmoles of N-pyruvoyl-L-Pro-ethyl ester, then 42 mmoles of sodium cyanoborohydride in ethanol is slowly added over the course of 6 hours. The reaction mixture is filtered and the solvent removed by a rotary evaporator, yielding the named compound.

EXAMPLE 54

Synthesis of N-[L-1-(dimethylaminoethyoxycarbonyl)-3-(carbonylmethylamino)propyl]-D,L-Ala-L-Pro ethylester By substituting 2-amino-4-carboxymethylamino-butyric acid dimethylaminoethyl ester for 2-amino-4-carboxyanilidobutyric acid N-acetylaminoethyl ester of Example 53, the named compound is synthesized.

EXAMPLE 55

A. By substituting L-proline-tert butyl ester for L-proline ethylester in Synthesis B of Example 1, the procedure of Synthesis B of Example 1 yields the pyruvoyl-L-Pro-tert-butyl ester.

The tert butyl ester can be removed by treatment with TFA in anisole.

B. A solution of 10 mmoles of Nα-Boc-S-benzyl-D-cysteineα-$NO_2$-phenyl ester in 3 ml of $CH_2Cl_2$ is added to a solution of 10.5 mmoles of any of the amine or imine compounds (listed in Table I, below) in 3 ml of $CH_2Cl_2$, and the resulting solution is stirred overnight at room temperature. The reaction is judged to be completed by thin layer chromatography. The resulting mixture is dissolved in 4 ml of TPA to remove the Boc blocking group, rotary evaporated and crystallized, to yield α-amides and α-imides of D-cysteine-α-benzyl ester as the product.

TABLE I: AMINE AND IMINE COMPOUNDS aniline
benzylamine
methylamine
ethylamine
1-aminopropane
2-aminopropane
2-aminobutane
t-butylamine
cyclopentylamine
cyclohexylamine
ε-aminocaproic acid benzyl ester
ε-aminocaproamide
3-amino-2-methyl-propionic acid ethyl ester
2-amino-propionic acid ethyl ester
glycine-t-butyl ester
valine-benzyl ester
p-OH-aniline
p-OH-m-iodo-aniline
p-carboxy-thienyl ester of aniline
m-F-benzylamine
4-OH-3,3'-Br-benzylamine
4-Cl-benzylamine
3,4-dichloro-benzylamine
3-$NO_2$-benzylamine
3-phenylpropylamine
2-indolylethylamine
2-amino-pyridine
adenine
cytidine
pyrroline
4-phenylbutylamine
α-methyl-alanine ethyl ester
3-hydroxy-propylamine
3-Boc-amino-propylamine
1-amino-3-hydroxy-butane
1-adamantanamine
2-adamantanamine
1-adamantanemethyl amine
$N^{\epsilon}$-Boc-lysine-ethyl ester
$N^{\alpha}$-Boc-lysine-t-butyl ester
$N^{g}$hydroxy-arginine-ethyl ester
$N^{g}$methyl-homoarginine-t-butyl ester
$N^{im}$-benzyl-histidine-t-butyl ester
leucine-t-butyl ester
isoleucine-t-butyl-ester
norvaline-ethyl ester
norleucine-methyl ester
glycine-p-methyl benzyl ester
α-methyl-alanine-dipenylmethyl ester
glycyl-benzylamide
α-methyl-alanyl-4-OH-benzylamide
$N^{im}$-benzyl-histidinyl-3-iodo-anilide
glycyl-pyrrolide
glycyl-1-adamantanamide
glutamine-ethyl ester
asparagine-t-butyl ester
α-methyl-valine-t-butyl ester
α-methyl-phenylalanine-t-butyl ester
tyrosine-t-butyl ester
O-benzyl-tyrosine-t-butyl ester
4-iodo-phenylalanine ethyl ester
3,5-dibromotyrosine-ethyl ester
thyronine-ethyl ester
vinyl glycine ethyl ester
β-fluoro-alanine ethyl ester
serine ethyl ester
threonine t-butyl ester
O-t-butyl-threonine-t-butyl ester
O-t-butyl-serine-ethyl ester
O-benzyl-serine-ethyl ester
O-methyl-serine-methyl ester
O-ethyl-serine-ethyl ester
S-ethyl-cysteine-ethyl ester
S-t-butyl-cysteine-t-butyl ester
S-benzyl-cysteine-t-butyl ester
S-benzyl-homocysteine-t-butyl ester
S-methyl-homocysteine ethyl ester
S-ethyl-homocysteine ethyl ester
S-t-butyl-homocysteine-t-butyl ester
O-t-butyl-homoserine-t-butyl ester
O-benzyl-homoserine-benzyl ester
O-methyl-homoserine-methyl ester
O-ethyl-homoserine-ethyl ester
O-phenyl-homoserine-ethyl ester
O-phenyl-serine-ethyl ester
S-phenyl-cysteine-ethyl ester
β-fluoro-phenylalanine ethyl ester
β-OH-phenylalanine-methyl ester
β-Br-alanine-methyl ester
β-thienylserine-t-butyl ester
3,5-dimethyl-tyrosine-t-butyl ester
β-hydroxynorvaline ethyl ester
β-benzyloxynorvaline-ethyl ester
$N^{\epsilon}$-Boc-hydroxylysine t-butyl ester
3-Boc-amino-tyrosine-ethyl ester
α-methyl-phenylalanine-ethyl ester
t-leucine methyl ester
α-methyl glutamine methyl ester
$N^{\epsilon}$-hydroxylysine t-butyl ester
β-N-methyl-lysine-methyl ester 5,5'-dihydroxy-leucine-ethyl ester
β-fluoro-asparagine-ethyl ester
β-methyl-asparagine-ethyl ester
γ-N-methyl-lysine-methyl ester
β-methyl-β-benzylamido-aspartic acid -α-ethyl ester
2-ethoxy-5-$NO_2$-phenylalanine ethyl ester
β-ethoxy-phenylalanine-t-butyl ester
α-methyl-serine-t-butyl ester
O-benzyl-α-methyl-serine-t-butyl ester
O-benzyl-α-methyl-serine-t-butyl ester C. Any of the α-amides or α-imides of D-cycteine-α-benzyl ester of Synthesis B of this example are then used to alkylate any of the α-keto carboxylic acids in Table II, immediately below. A quantity of 5 mmoles of any of the α-amides or α-imides of D-cysteine-α-benzyl ester of Synthesis B is dissolved in 1 ml of ethanol and added with stirring to 5 mmoles of $NaHCO_2$ in 0.2 ml $H_2O$. To the resulting solution is added 25 mmoles of any α-keto carboxylic acid of Table II in 2 ml of ethanol plus 1.6 g of molecular sieves. The mixture is stirred for 1 hour at room temperature, then 5 mmoles of sodium cyanoborohydride, in 1.5 ml of ethanol, is added drop-wise over a period of 4 hrs. The reaction mixture is left at room temperature overnight. After filtration, solvent is removed from the filtrate, and the product purified by column chromatography. The products are compounds of the formula:

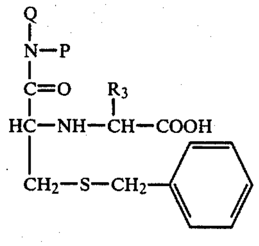

TABLE II: α KETO CARBOXYLIC ACIDS pyruvic acid
phenylpyruvic acid
3-cyclohexyl-2-oxopropionic acid (cyclohexylpyruvic acid)
6-methyl-2-oxoheptanoic acid
4-methyl-2-oxoheptanoic acid
2-oxobutyric acid
3-methyl-2-oxobutyric acid
2-oxoglutaric acid
2-oxoadipic acid
2-oxo-4-phenylbutyric acid (and its t-butyl ester)
4-(3-indolyl)-2-oxobutyric acid
N-acetylaminoethyl-2-oxo-4-phenylbutyrate
dimethylaminoethyl-2-oxo-4-phenylbutyrate
2-oxo-5-methylhexonic acid
phenoxypyruvic acid
phenylthiopyruvic acid
4-p-chlorophenyl-2-oxobutyric acid
indole-3-pyruvic acid
2-oxo-3-p-cyanophenylpropionic acid
4-α-naphthyl-2-oxobutyric acid
4-(3,4-dichlorophenyl)-2-oxo-butyric acid
2-oxo-4-p-phenoxyphenylbutyric acid D. Any of the products of Synthesis C of this example are reacted with L-proline ethyl ester, or L-proline-tert butyl ester or an α-ethyl ester of any of the L-proline analogs listed in Table III, immediately below. The reaction is carried out according to the coupling procedures of Synthesis B of Example 1 or Synthesis A of Example 51.

TABLE III 3,4-dehydroproline
4,5-dehydroproline
3,4-di-OH-proline
3-methoxyproline
3,4-dimethoxy proline
4-fluoro-proline
3-fluoro-proline
3-methoxyproline
3,4-dimethoxyproline
4-fluoro-proline
3-fluoro-proline
3,4-fluoroproline
4-Cl-proline
3-Cl-proline
3,4-dichloro-proline
3-Br-proline
3,4-dibromo-proline
4-iodo-proline
3-iodo-proline
3,4-diiodo-proline
5-phenyl-thioproline
5-hydroxyphenyl-thioproline (o-, m- or p-)
4-mercapto-proline-proline
3-mercapto-proline
4-methylthio-proline
3-methylthio-proline
4-aminomethyl-proline
3-aminomethyl-proline
β-thioproline
α-methyl-proline
3-OH-5-methyl-proline
4-methylene proline
4-hydroxymethyl-proline
4-propyl-proline
3-propyl-proline
L-proline
L-pyroglutamic acid
4-keto-L-proline
3-keto-L-proline
4-hydroxy-L-proline
3-hydroxy-L-proline
L-pipecolic acid
4-methoxy-L-proline
4-bromo-L-proline
L-thiazolidine-4-carboxylic acid
L-2-azetidine carboxylic acid Products of Synthesis D of this example are saponified to remove the ethyl ester. They are treated with anhydrous HF in the presence of anisole to remove the S-benzyl protecting group. If the ethyl ester or benzyl ester groups are removed, the final product of Synthesis D of this example has the formula:

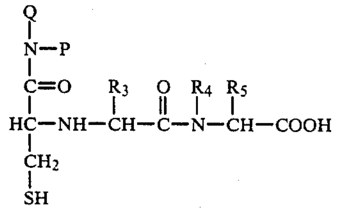

EXAMPLE 56

By substituting $N^{\alpha}$-Boc-S-benzyl-D-homocysteine-α-$NO_2$-phenyl ester for $N^{\alpha}$-Boc-S-benzyl-D-cysteine-α-$NO_2$-phenyl ester of Synthesis B of Example 55, and following the procedures of Example 55, compounds of the formula

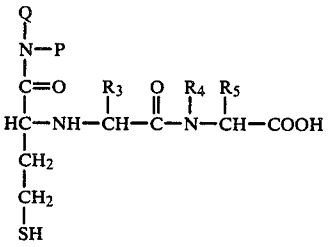

are obtained.

EXAMPLE 57

By substituting $N^{\alpha}$-Boc-D-aspartic acid-α-$NO_2$-phenyl ester-β-ethyl ester for Nα-Boc-S-benzyl-D-cysteine-α-$NO_2$-phenyl ester of Synthesis B in Example 55, and following the procedure of Example 55, with selected deprotection steps, compounds of the formula:

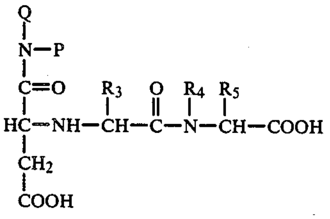

are obtained.

What is claimed is:

1. Novel compounds of the general formula:

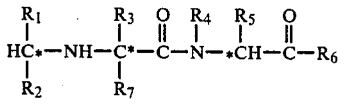

where $R_2$ is COOH, $CH_2COOH$, COSH, $CH_2COSH$, $CH_2SH$, $CH_2CH_2SH$, a physiologically acceptable nontoxic salt of any of them;

COOY, $CH_2COOY$, COSY, $CH_2SY$, or $CH_2CH_2SY$ wherein Y is phenyl, benzyl or a 1-5 carbon alkyl group; or

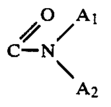

wherein either of $A_1$ and $A_2$ may be H, phenyl, benzyl or a 1-5 carbon alkyl group;

$R_4$ and $R_5$ together form a ring with the nitrogen and carbon atoms to which they are respectively attached, which ring is one of the structures:

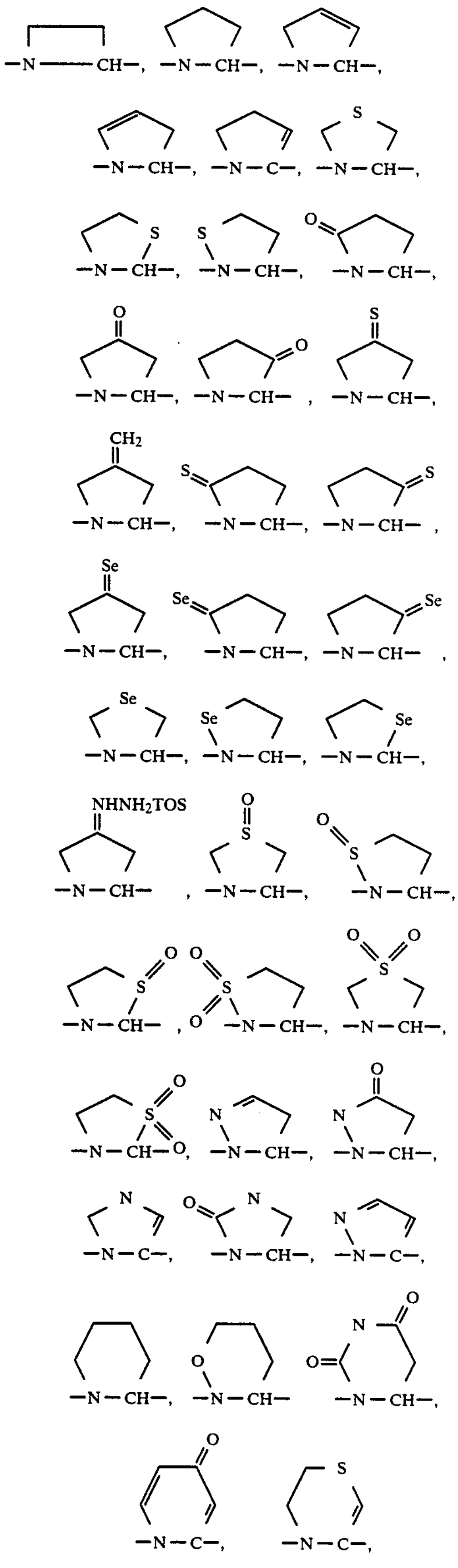

-continued

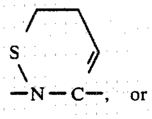 or 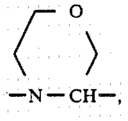

it being understood that any of these structures may be monosubstituted with —OH, —$OCH_3$, F,

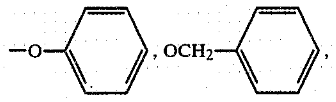

Cl, Br, I, phenyl, hydroxyphenyl, —SH, —$SCH_3$,

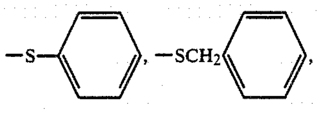

—$NHCH_3$, —$CH_2NH_2$, —$CH_3$, —$CH_2OH$, propyl, guanidino, nitro guanidino or thioguanidino and that any of the 5- or 6-membered rings may be disubstituted with —OH, F, Cl, Br, I, $OCH_6$ or any combination of two of this group of substituents;

$R_6$ is —OM or —SM, wherein M may be H, an alkyl group of 1–3 carbon atoms or any other ester moiety hydrolyzable under mammalian in vivo conditions to —OH, or an ionically bonded anion of a physiologically acceptable nontoxic salt;

$R_7$ is H—, $CH_3$—, halomethyl, hydroxymethyl, aminomethyl or mercaptomethyl; and A. $R_1$ and $R_3$ may each be of the general formula

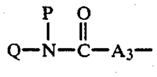

wherein $A_3$ is:

I. alkylene of 1–6 carbons, branched chain alkyl of 1–6 carbons, cycloalkyl alkylene, alkylcycloalkylalkylene, or alkylcycloalkylene;

II. aralkylene wherein the alkyl group is 1–6 carbons or alkylaryl;

III. phenyl;

IV. alkylaralkylene wherein the alkyl groups may be the same or different and are 1–6 carbons in length;

V. substituted alkylene, substituted branched chain alkyl, substituted cycloalkylalkylene, substituted alkyl cycloalkylalkylene, substituted alkylcycloalkylene, substituted alkylaryl, substituted aralkylene, substituted phenyl or substituted alkylaralkylene wherein the substituent or substituents may be the same or different, may be included in an alkylene chain or pendent thereto, and are selected from amino, halo, hydroxy, mercapto, $NO_2$, carboxy, $CONH_2$, lower alkyl, halomethyl, hydroxymethyl, aminomethyl, dihalomethyl, trihalomethyl, cyano, mercaptomethyl, methoxymethyl, methylthiomethyl, methoxycarbonylmethyl, cyanomethyl, benzyl, acetoxymethyl, $CH_2$=CH—$CH_2$—, isobutyl mercaptoalkyl of 2–3 carbon atoms, hydroxyalkyl of 2–3 carbons atoms, acetylthioethyl, benzamido, acetamido, phthaloylaminoalkylene wherein the alkylene group has 1–4 carbon atoms, α-alkoxycarbonyl isoalkylene wherein the alkyl group contains 1–5 carbons and the isoalkylene group contains 3–5 carbons, benzoylamino, alkanoylamino of 1–5 carbons, alkylamide of 1–5 carbons, phenylamine, alkylamine of 1–5 carbons, lower alkoxy, aryloxy, lower alkylamino, diloweralkylamino, acylamino, arylamino, guanidino, imidazolyl, indolyl, lower alkylthio, arylthio, carboxy amido and carbolower alkoxy;

VI. alkylenethio- or alkylenethioalkylene of 1–6 carbons, alkylthioalkylene of 1–6 carbons;

VII. alkyleneoxy or alkyleneoxyalkylene wherein the alkyl groups may be the same or different and are 1–6 carbons;

VIII. alkoxyphenyl or alkoxybenzyl in which the alkoxy groups has 1–3 carbons, phenoxyphenyl, phenoxybenzyl, benzyloxybenzyl or benzloxyphenyl or a thioether analog of any of them:

IX.

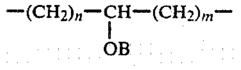

wherein n=0–4, m=0–4, and

B=H or a 1–5 carbon alkyl group; or an —SB analog thereof;

X.

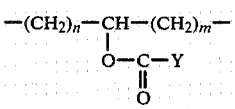 or 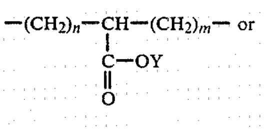 or

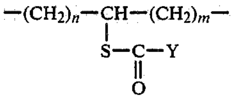 or 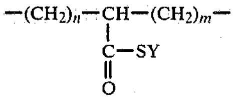

wherein n and m have the same significance as above, Y is phenyl, benzyl or a 1–5 carbon alkyl group;

XI.

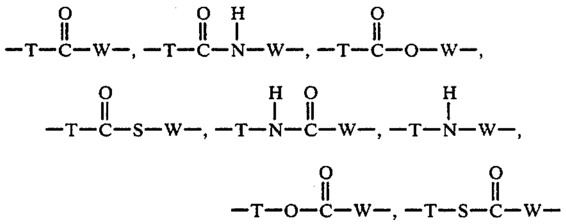

wherein T and W may be the same or different and are alkylene, aryl, benzyl or cycloalkyl; and P and Q may be the same, or one of them may be H or they may combine to form a ring with the nitrogen to which they are attached;

either or both of P and Q may be selected from any of the following:

(a) $C_1$–$C_6$ straight or branched chain alkyl groups or $C_1$–$C_6$ straight or branched chain alkenyl groups, any one of which may be substituted with any of halo, hydroxy, alkoxy, arloxy, amino, alkylamino, dialkylamino, alkylacylamino, arylamino, guanidino, thioguanidino, nitroguanidino, hydrazino, ureido, nitro, mercaptocarbonyl, hydroxyamino, histidinyl, cyano, imidazolyl, indolyl, mercapto, alkythio, arylthio, carboxy, amido or carboalkoxy, wherein the alkyl groups containg 1-6 carbon atoms;

(b) cycloalkyl or cycloalkyl alkylene wherein cycloalkyl has 4–12 carbons, and alkylene 1–5 carbons, which may be substituted with any of —OH, —SH, halo, —COOH, —COSH, $CONH_2$, $—NO_2NH_2$, $—NO_2$, $—CH_3$, $—OCH_3$,

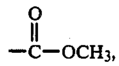

hydrazino, ureido, $—SCH_3$, hydroxyamino, cyano, guanidino, thioguanidino or nitroguanidino groups;

(c) aralkyl or alkaryl groups which may be ring substituted with one or more of the following:

SH, halo, $CH_2COOH$, $CH_2CONH_2$, $CH_2CONH$-alkyl, COSH, COOH, $CONH_2$, CONH-alkyl, $CH_2COSH$, $CH_2SH$, $CH_2OH$, OH, $NO_2$, amino alkyl, alkoxy, aralkyloxy, alkylthio, and aralkylthio groups, wherein the alkyl groups contain 1-6 carbons and may also alternatively be chain substituted with $—CH_3$, —OH, $—OCH_3$, halo, $—SCH_3$,

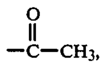

$—NH_2$, $—NO_2$, —CN, —SH, $—NHNH_2$,

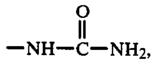

—NHOH or a thio or nitro derivative thereof, —COOH or —COSH;

(d) an aryl, heterocyclic or adamantanyl group which may be ring-substituted with at least one group selected from halo, —OH, —O—alkyl, —O—aryl, $—NH_2$, —NH—alkyl, $—N—(alkyl)_2$,

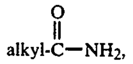

aryl—$NH_2$, guanidino, thioguanidino, nitroguanidino, hydrazino, ureido, nitro, mercaptocarbonyl, hydroxyamino, cyano imidazolyl, indanyl, histidinyl, —SH, —S—alkyl, S—aryl,

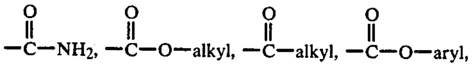

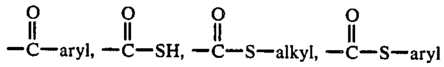

and $—NO_2$; when P and Q join with N to form a ring, the ring may be any 4–10 membered heterocyclic ring which contains a nitrogen with only two of its valences attached to other ring members;

B. alternatively $R_1$ may be

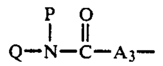

and $R_3$ may be (i) mono-N substituted alkylene of 2–4 carbons wherein the N substituent is benzoyl, Boc, CbO, Tos, formyl or acetyl;

(ii) hydroxphenyl or hydroxyphenyl-(1-6C)-alkylene or a thiol analog of either;

(iii) mercaptoalkylene of 1–6 carbons;

(iv) phenylalkylene wherein the alkylene group has 1–6 carbons;

(v) phenylthioalkylene or benzylthioalkylene wherein the alkylene group has 1–6 carbons;

(vi) alkylthioalkylene wherein the alkyl and alkylene groups have 1–3 carbons;

(vii) alkoxyphenyl or alkoxybenzyl in which the alkoxy group has 1–3 carbons, phenoxyphenyl, phenoxybenzyl, benzyloxybenzyl or benzyloxphenyl or a thioether analog of any of them.

(viii)

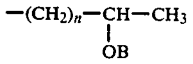

wherein n=0–4 and B=H or a 1–6 carbon alkyl group, or an —SB analog thereof;

(ix) $(CH_2)_pCOOZ$ or $(CH_2)_pCOSZ$ wherein p=0-3 and Z is H, phenyl, benzyl, a 1-5 carbon alkyl group, or an anion of a physiologically acceptable salt;

(x)

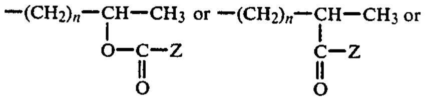

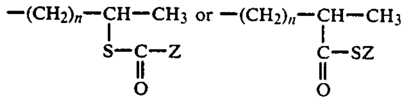

wherein n is 0 to 4 and Z each have the same significance as above:

(xi)

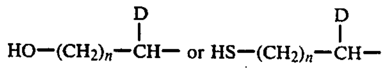

wherein n=0–4, D is phenyl, thienyl or a 1–3 carbon alkyl group;

(xii) $HO—(CH_2)_n—C(CH_3)_2—$, $HS—(CH_2)_n—C(CH_3)_2—$, p-hydroxyphenyl—$(CH_2)_n—C(CH_3)_2—$ or —p-mercaptophenyl—$(CH_2)_n—C(CH_3)_2—$ wherein n has the same significance as above;

(xiii) p-mercaptophenyl—$(CH_2)_n—CH_2—$ or p-hydroxyphenyl—$(CH_2)_n—CH_{2LL}$—wherein the phenyl ring has one or two nitro or amino substituents and n has the same significance as above;

(xiv)

$$CH_3(CH_2)_n-\overset{OH}{\overset{|}{CH}}- \text{ or } CH_3(CH_2)_n-\overset{SH}{\overset{|}{CH}}-$$

wherein n has the same significance as above;

(xv) $NH_2$—alkylene or $NO_2$—alkylene containing one hydroxy or mercapto substituent and having 1-6 carbon atoms;

(xvi) hydroxy- or mercapto-phenoxybenzyl;

(xvii)

$$ZO(CH_2)_q-\overset{O}{\overset{\|}{C}}-(CH_2)_n-,\ ZS-(CH_2)_q-\overset{O}{\overset{\|}{C}}-(CH_2)_n-,$$

$$NH_2-(CH_2)_q-\overset{O}{\overset{\|}{C}}-(CH_2)_n-,\ NO_2(CH_2)_q-\overset{O}{\overset{\|}{C}}-(CH_2)_n-,$$

$$HONH-(CH_2)_q-\overset{O}{\overset{\|}{C}}-(CH_2)_n-,$$

$$NH_2NH-(CH_2)_q-\overset{O}{\overset{\|}{C}}-(CH_2)_n-,\ ZO-\overset{O}{\overset{\|}{C}}(CH_2)_q-\overset{O}{\overset{\|}{C}}(CH_2)_n-,$$

$$ZS-\overset{O}{\overset{\|}{C}}-(CH_2)_q-\overset{O}{\overset{\|}{C}}-(CH_2)_n \text{ or}$$

$$NH_2\overset{O}{\overset{\|}{C}}NH-(CH_2)_q-\overset{O}{\overset{\|}{C}}-(CH_2)_n-$$

wherein q=1-5 and n is from 0 to 4 and Z has the same significance as above:

(xviii)

$$ZO-(CH_2)_q-\overset{OH}{\overset{|}{CH}}-(CH_2)_n-,\ ZS-(CH_2)_q-\overset{OH}{\overset{|}{CH}}-(CH_2)_n,$$

$$NH_2-(CH_2)_q-\overset{OH}{\overset{|}{CH}}-(CH_2)_n-,\ NO_2-(CH_2)_q-\overset{OH}{\overset{|}{CH}}-(CH_2)_n-,$$

$$NH_2-\overset{O}{\overset{\|}{C}}-NH-(CH_2)_q-\overset{OH}{\overset{|}{CH}}-(CH_2)_n-,$$

$$ZO-(CH_2)_q-\overset{OH}{\overset{|}{CH}}-(CH_2)_n-,\ ZS-(CH_2)_q-\overset{OH}{\overset{|}{CH}}-(CH_2)_n-,$$

$$HONH-(CH_2)_q-\overset{OH}{\overset{|}{CH}}-(CH_2)_n-, \text{ or}$$

$$NH_2NH-(CH_2)_q-\overset{OH}{\overset{|}{CH}}-(CH_2)_n-,$$

wherein q and n all have the same significance as above;

(xix)

$$G-NH-(CH_2)_q-\overset{O}{\overset{\|}{C}}-(CH_2)_n-,\ G-NH(CH_2)_q-\overset{OH}{\overset{|}{CH}}-(CH_2)_n,$$

$$G-(CH_2)_q-\overset{O}{\overset{\|}{C}}-(CH_2)_n-,\ G-(CH_2)_q-\overset{OH}{\overset{|}{CH}}-(CH_2)_n-,$$

$$NH_2-\underset{O}{\underset{\|}{C}}-(CH_2)_q-\underset{O}{\underset{\|}{C}}-(CH_2)_n-, \text{ or}$$

-continued $$-NH_2-\overset{O}{\overset{\|}{C}}-(CH_2)_q\overset{OH}{\overset{|}{CH}}-(CH_2)_n-,$$

wherein G is an alkacyl or alkacyloxy group of 1-6 carbons, a benzoyl or a benzoyloxy group, or a phenylalkacyl or phenylalkacyloxy group wherein the alkacyl or alkacyloxy group contains 2-6 carbons and q and n have the same significance as set forth above;

(xx)

$$K-(CH_2)_n-\overset{O}{\overset{\|}{C}}-(CH_2)_n- \text{ or } K-(CH_2)_n-\overset{OH}{\overset{|}{CH}}-(CH_2)_n-$$

wherein n has the significance stated above and K is selected from carboxyphenyl, aminophenyl, nitrophenyl, halophenyl, hydroxyphenyl, alkylthiophenyl, alkylphenyl, mercaptophenyl, cyanophenyl, mercapto-carbonyphenyl, alkylcarbonyphenyl, alkycarbonyloxyphenyl, hydrazinophenyl, ureidophenyl, alkylcarbonylaminophenyl, alkylcarbonylthiophenyl, alkyloxylphenyl and hydroxyaminophenyl, wherein all alkyl groups contain 1-6 carbon atoms;

(xxi)

$$L-(CH_2)_n-\overset{O}{\overset{\|}{C}}-(CH_2)_n- \text{ or } L-(CH_2)_n-\overset{OH}{\overset{|}{CH}}-(CH_2)_n-$$

wherein n has the significance stated above and L is selected from cycloalkyl groups of 3-7 carbons which may be unsubstituted or substituted with up to two groups selected from among carboxy, amino, nitro, halo, hydroxy, mercapto, mercaptocarbonyl, hydroxyamino, alkyl, alkylcarbonyl, alkylcarbonyloxy, alkylthio, alkylcarbonylamino, alkycarbonylthio, cyanohydrazino, ureido and alkyloxy, wherein all alkyl groups contain 1-6 carbon atoms;

(xxii) guanidino alkylene, thioguanidinoalkylene, or nitroguanidino alkylene in which the alkylene groups contain 1-6 carbon atoms;

(xxiii) ring substituted aryl groups in which the ring substituents may be the same or different and may comprise up to five per ring of the following: $-NH_2$, $-OZ$, $-SZ$, halogen, $-CN$, $-NO_2$, $-COOZ$, $-COSZ$, $-COHN_2$, $-NHNH_2$, alkyl, alkylcarbonyl, alkylcarbonyloxy, alkylcarbonylamino, haloalkyl, dihaloalkyl, trihalomethyl, hydroxyamino, alkylcarbonylthio, phenoxy, and benzyloxy wherein the alkyl groups contain 1-6 carbon atoms and Z has the same significance as above;

(xxiv) amidoalkylene or alkylcarbonyl-aminoalkylene wherein the alkyl and alkylene groups contain 1-6 carbon atoms;

(xxv) hydroxyaminoalkylene of 1-6 carbons;

(xxvi) vinyl and substituted vinyl groups in which the substituents may be alkyl, aryl, cycloalkyl or hetrocyclic groups;

(xxvii) unsubstituted heterocyclic groups from among phenothiazinyl, pyrrolidinyl, pyrrolyl, quinolinyl, imidazolyl, pyridyl, thyminyl, benzothiazinyl, indolyl, thienyl, purinyl, piperidinyl, morpholinyl, azaindolyl, pyrazinyl, pyrimidyl, piperonyl, piperazinyl, furanyl, thiazolyl and thiazolidinyl, cystosinyl;

(xxviii) alkylene or alkenyl groups 1-6 carbons substituted with one of the heterocyclic rings from (xxvii) above;

(xxix) groups from (xxvii) or (xxviii) above containing up to four ring substituents on the heterocyclic ring selected from among —OZ, —SZ, —COOZ, $—NO_2$, $—NH_2$, —COSZ, halogen, haloalkyl, dihaloalkyl, trihalomethyl, cyano, $CONH_2$, alkyl, alkylcarbonyl, alkylcarbonyloxy, alkylcarbonylamino, alkyl-carbonylthio, phenoxy, benzyloxy,

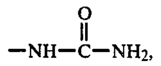

$—NHNH_2$ and HONH—, wherein Z has the same significance as above;

(xxx) groups from (xxvii), (xxviii) or (xxix) attached to one valence of an etheric —O— or —S—;

(xxxi) mono-, di- or tri-alkyl, alkenyl- or phenyl-silyl or -selenyl wherein the alkyl or alkenyl groups contain 1-6 carbons;

(xxxii) any of H, 1-5 carbon straight or branched chain alkyl, phenyl, —OH, alkoxy of 1-6 carbons, benzyloxy, benzyloxyalkylene or phenoxyalkylene wherein the alkylene has 1-5 carbons, alkoxyalkylene having 1-5 carbons in the alkoxy and alkelene groups, aminoalkylene of 1-6 carbons, alkenyl of 1-6 carbons, benzyl, hydroxyalkyl of 1-6 carbons, mercaptoalkyl of 1-6 carbons, histidinyl, haloalkyl of 1-6 carbons, 4-aminomethyl-benzyl, acetamidoalkyl of 1-5 carbons, benzylthiomethylene, or dimethylaminoalkyl of 1-5 carbons;

C. alternatively, $R_3$ may be

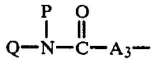

and $R_1$ may be any of groups (i)-(xxxii) above or any of H, $C_1$-$C_8$ straight or branched chain alkyl, phenyl, benzyl, unsubstituted aminoalkylene of 2-6 carbons, hydroxyalkylene of 1-6 carbons, hydroxphenyl, phenoxyalkylene or benzyloxyalkylene wherein the alkylene group has 1-6 carbons, cycloalkyl of 3-6 carbons, cycloalkyl methyl, 3-indolyl, phenylethyl, methylthioethyl, 3-indolyl alkyl wherein the alkyl group contains 1-5 carbons, imidazolyl, imidazolyalkyl wherein the alkyl group contains 1-5 carbons, phenoxymethyl, phenylthiomethyl, 4-aminomethyl benzyl, 2-aminophenethyl, naphthylethyl, 4-halophenethyl, 3,4-dihalophenethyl or phenoxyphenethyl, or $R_1$ and $R_2$ together may form with —CH a lactone ring of the formula:

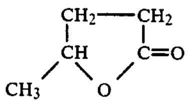 or 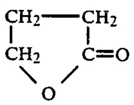

or an analogous six-membered ring.

2. A compound according to claim 1 wherein $R_1$ and $R_3$ are each of the general formula

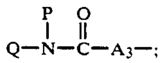

$A_3$ is a radical of groups (I)-(XI);

P and Q may be the same, or one of them may be H or they may combine to form a ring with the nitrogen to which they are attached, wherein P and Q may be selected from any of the radicals of the groups (a)-(d).

3. A compound according to claim 1 wherein P=H, Q=iodo-phenyl, $A_3$ is the radical $—(CH_2CH_2)—$, $R_3=CH_3$, $R_4$ and $R_5$ together form the structure

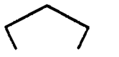

$R_6$=OH, $R_7$=H and $R_2$=COOH, or physiologically acceptable salts thereof.

4. A compound according to claim 1 wherein P=H, Q=phenyl, $A_3$ is the radical $—(CH_2CH_2)—$, $R_3=CH_3$, $R_4$ and $R_5$ together form the structure

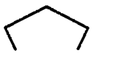

$R_6$=OH, $R_7$=H and $R_2$=COOH, or physiologically acceptable salts thereof.

5. A compound according to claim 1 wherein P=H, Q=iodo-phenyl, $A_3$ is the radical $—(CH_2CH_2)—$, $R_3=CH_3$, $R_4$ and $R_5$ together form the structure

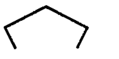

$R_6$=OH, $R_7$=H and $R_2$=

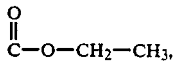

or physiologically acceptable salts thereof.

6. A compound according to claim 1 wherein P=H, Q=phenyl, $A_3$ is the radical $—(CH_2CH_2)—$, $R_3=CH_3$, $R_4$ and $R_5$ together form the structure

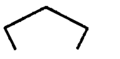

$R_6$=OH, $R_7$=H and $R_2$=

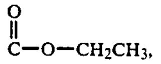

or physiologically acceptable salts thereof.

7. A compound according to any of claims 1-2 wherein P-N-Q forms structures selected from the group consisting of anilino, benzylamino, 2-amino pyridyl amino, 3-amino pyridyl amino, 4-amino pyridyl amino, 3-indolyl amino, and histamino.

8. A compound according to claim 1 wherein $R_1$ is

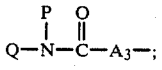

and $R_3$ is phenyloxyalkylene, benzyloxyalkylene, benzylalkyleneoxyalkylene, wherein the alkylene group has 1-5 carbons.

9. A compound according to claim 1 wherein $R_1$ is phenyloxyalkylene, benzyloxyalkylene, benzylalkylene oxyalkylene, wherein the alkylene group has 1-5 carbons; and $R_3$ is

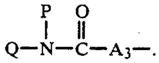

10. A compound according to claim 1 wherein $R_2$ forms a physiologically acceptable ester.

11. A compound according to any of claim 1 wherein $R_2$ is $COOC_2H_5$.

12. A composition of matter effective to inhibit angiotensin converting enzyme in vivo which contains as its essential active ingredient a therapeutically effective amount of a compound of any of claims 1-11.

13. A composition of matter for reducing the blood pressure in vivo of a mammal in a hypertensive state which contains as its essential active ingredient a therapeutically effective amount of a compound of any of claims 1-11.

14. A method for inhibiting angiotensin converting enzyme in vivo which comprises administering to a mammal showing an abnormal serum level of angiotensin II a therapeutically effective dose of a compound of any of claims 1-11.

15. A method for reducing the blood pressure of a mammal in a hypertensive state which comprises administering to such mammal a therapeutically effective dose of a compound of any of claims 1-11.

* * * * *